(12) United States Patent
Fukushima et al.

(10) Patent No.: US 8,889,699 B2
(45) Date of Patent: Nov. 18, 2014

(54) 5-FLUOROURACIL DERIVATIVE

(75) Inventors: Masakazu Fukushima, Shiga (JP); Shozo Yamada, Tokushima (JP); Ryo Oyama, Saitama (JP)

(73) Assignee: Delta-Fly Pharma, Inc., Tokushima (JP)

( * ) Notice: Subject to any disclaimer, the term of this patent is extended or adjusted under 35 U.S.C. 154(b) by 103 days.

(21) Appl. No.: 13/419,691

(22) Filed: Mar. 14, 2012

(65) Prior Publication Data

US 2012/0232103 A1  Sep. 13, 2012

Related U.S. Application Data

(63) Continuation-in-part of application No. PCT/JP2010/068895, filed on Oct. 26, 2010.

(30) Foreign Application Priority Data

Oct. 27, 2009 (JP) ................................ 2009-246400

(51) Int. Cl.
*C07D 401/14* (2006.01)
*A61K 31/513* (2006.01)

(52) U.S. Cl.
CPC .................... *C07D 401/14* (2013.01)
USPC ........................... 514/274; 544/301

(58) Field of Classification Search
USPC .......................... 544/310; 514/274
See application file for complete search history.

(56) References Cited

U.S. PATENT DOCUMENTS 5,047,521 A  9/1991  Fujii et al.

FOREIGN PATENT DOCUMENTS

| GB | 2 192 880 | 1/1988 |
| JP | 63-201127 | 8/1988 |
| JP | 63-301880 | 12/1988 |
| WO | 87/06582 | 11/1987 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer, 84(10):1424-1431,2001.*
Gura et al., Systems for identifying new drugs are often faulty, Science, 278:1041-1042, 1997.*
Simone, Oncology: Introduction, Cecil Textbook of Medicine, 20th Editino, vol. 1, pp. 1004-1010, 1996.*
Cao et al., Differential Expression of uridine phosphorylase in tumors contributes to an improved fluoropyrimidine therapeutic activity, Mol Cancer Ther. 10(12):2330-2339, Dec. 2011, pp. 1-20.*
International Search Report issued Dec. 7, 2010 in International (PCT) Application No. PCT/JP2010/068895.

* cited by examiner

*Primary Examiner* — Deepak Rao
(74) *Attorney, Agent, or Firm* — Wenderoth, Lind & Ponack, L.L.P.

(57) ABSTRACT

The present invention provides a novel antimetabolic anticancer agent that has an excellent balance between antitumor effect and toxicity. Specifically, the present invention provides a medicament containing, as an active ingredient, a 5-fluorouracil derivative represented by Formula (I) or a salt thereof:

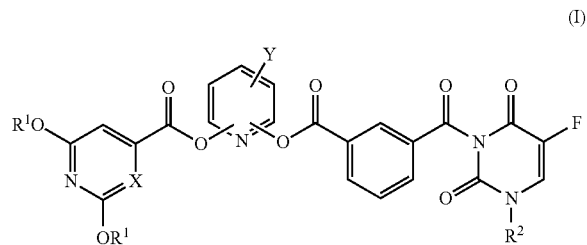

wherein $R^1$ represents a hydrogen atom or a protecting group of a hydroxy group, $R^2$ represents a lower alkoxy-lower alkyl group or a tetrahydrofuranyl group, X represents a carbon atom or a nitrogen atom, and Y represents a halogen atom or a cyano group.

9 Claims, 2 Drawing Sheets

5-FLUOROURACIL DERIVATIVE

This application is a CIP of International Application No. PCT/JP2010/068895 filed Oct. 26, 2010.

TECHNICAL FIELD

A Cross Reference of Related Applications

This application claims priority to JP No. 2009-246400 filed on Oct. 27, 2009, the entire contents of which are incorporated by reference herein.

The present invention relates to a novel 5-fluorouracil derivative or a salt thereof, and the use thereof.

BACKGROUND ART

5-Fluorouracil (hereinafter referred to as 5-FU) is widely used in treating various cancers, mainly gastrointestinal cancers, singly or in combination with other anticancer agents. However, 5-FU itself has only a weak antitumor effect and causes various side effects, such as diarrhea, stomatitis and others due to gastrointestinal toxicity, and myelosuppression. Therefore, it is difficult to say that 5-FU is always easy to use for cancer patients. To solve these problems, various orally administered 5-FU derivatives are under development; however, satisfactory clinical effects have not yet been obtained. The probable reasons for that are as follows. 5-FU is promptly decomposed in vivo by dihydropyrimidine dehydrogenase (hereinafter referred to as DPD), which is contained, in particular, in liver and tumor tissues; therefore, it is difficult to attain a sufficient antitumor effect corresponding to its dosage. 5-FU is uptaken not only into cancer cells but also into normal cells, such as marrow cells and gastrointestinal mucosa cells, and converted to active metabolites by the action of orotate phosphoribosyl trasnferase (hereinafter referred to as OPRT). Such active metabolites cause cell damage, i.e., they have cytotoxicity; therefore, their antitumor effect and side effects are not well balanced.

Compounds having a DPD inhibitory activity and an antitumor activity have been reported as examples of 5-FU derivatives (see patent literature 1 to 3). Among these, PLT 2 specifically discloses Compound (1) shown below, which is a compound generally known as Emitefur (also referred to as BOF-A2). A clinical trial was conducted to evaluate Emitefur; however, its development was discontinued, since it had strong side effects.

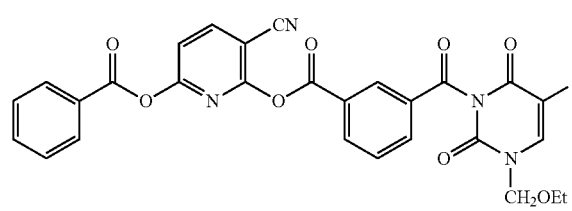

(1)

As described above, 5-FU derivatives that can enhance the antitumor effect by suppressing the decomposition of 5-FU in vivo and, at the same time, reduce the side effects have not yet been developed. Therefore, it is necessary to develop a novel 5-FU derivative having an enhanced antitumor-effect and low toxicity to improve the therapeutic effect for treating cancer patients.

As described above, there have been no reports about a derivative having an antitumor activity in addition to a DPD inhibitory activity and an OPRT inhibitory activity in one compound. Therefore, the development of a drug that achieves a balance between effects and toxicity, i.e., having a strong antitumor effect on human cancers and reduced gastrointestinal damage, and that improves the QOL of cancer patients is demanded.

CITATION LIST

Patent Literature

PTL 1: Japanese Unexamined Patent Publication No. S63-201127
PTL 2: Japanese Unexamined Patent Publication No. S 63-301880 PTL 3: WO87/06582

SUMMARY OF INVENTION

Technical Problem

An object of the present invention is to provide a novel antimetabolic anticancer agent exhibiting a strong antitumor effect on tumor cells while reducing damage to the gastrointestinal tract, i.e., having well balanced effects and toxicity, by possessing a DPD inhibitory activity as well as an OPRT inhibitory activity in vivo.

Solution to Problem

The present inventors have conducted extensive research to solve the above problem. As a result, they found that the 5-fluorouracil derivative represented by Formula (I) below (hereinafter also referred to as Compound (I) of the present invention) or a salt thereof has (1) DPD inhibitory activity and (2) OPRT inhibitory activity, and, as a result, (3) achieves a balance between a strong antitumor effect and reduced gastrointestinal damage, i.e., it is superior to known 5-FU derivatives in terms of the balance between effects and toxicity.

The present invention has been accomplished based on these findings.

More specifically, the present invention provides the following items:

Item 1. A 5-fluorouracil derivative represented by Formula (I) below or a salt thereof:

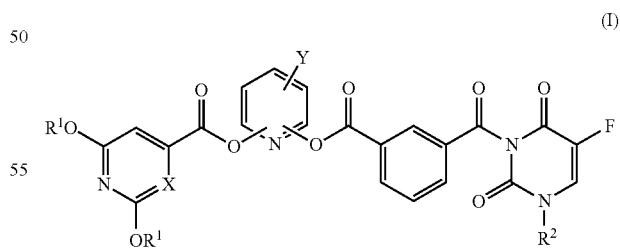

(I)

wherein $R^1$ represents a hydrogen atom or a protecting group of a hydroxy group, $R^2$ represents a lower alkoxy-lower alkyl group or a tetrahydrofuranyl group, X represents a carbon atom or a nitrogen atom, and Y represents a halogen atom or a cyano group.

Item 2. The 5-fluorouracil derivative or a salt thereof according to Item 1, wherein the group represented by the following formula in Formula (I) is:

a group represented by:

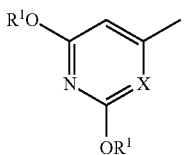

a group represented by:

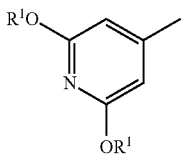

wherein $R^1$ represents a hydrogen atom, an allyl group, or a substituted or unsubstituted benzyl group,
a group represented by:

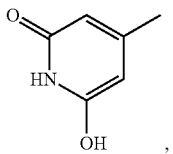

a group represented by:

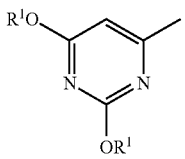

wherein $R^1$ represents a hydrogen atom, an allyl group, or a substituted or unsubstituted benzyl group, or
a group represented by:

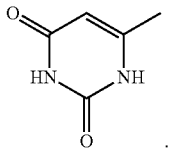

Item 3. The 5-fluorouracil derivative or a salt thereof according to Item 1 or 2, wherein $R^1$ represents a hydrogen atom, an allyl group, a benzyl group, an aliphatic acyl group, an aromatic acyl group, or an alicyclic acyl group, $R^2$ represents a lower alkoxymethyl group in which the lower alkoxy moiety has 1 to 6 carbon atoms or a tetrahydrofuranyl group, X represents a carbon atom or a nitrogen atom, and Y represents a fluorine atom or a chlorine atom.

Item 4. The 5-fluorouracil derivative or a salt thereof according to any one of Items 1 to 3, wherein $R^1$ represents a hydrogen atom, a benzyl group, an acetyl group, a propionyl group, an isobutyryl group, a pivaloyl group, a benzoyl group, p-chlorobenzoyl, or a cyclopentanecarbonyl group, $R^2$ represents a lower alkoxymethyl group in which the lower alkoxy moiety has 1 to 6 carbon atoms, X represents a carbon atom or a nitrogen atom, and Y represents a fluorine atom or a chlorine atom.

Item 5. The 5-fluorouracil derivative or a salt thereof according to any one of Items 1 to 4, wherein $R^1$ represents a hydrogen atom, an acetyl group, or a propionyl group, $R^2$ represents a lower alkoxymethyl group in which the lower alkoxy moiety has 1 to 6 carbon atoms, X represents a carbon atom or a nitrogen atom, and Y represents a chlorine atom.

Item 6. The 5-fluorouracil derivative or a salt thereof according to any one of Items 1 to 5, wherein $R^1$ represents a hydrogen atom, an acetyl group, or a propionyl group, $R^2$ represents a lower alkoxymethyl group in which the lower alkoxy moiety has 1 to 6 carbon atoms, X represents a carbon atom, and Y represents a chlorine atom.

Item 7. The 5-fluorouracil derivative or a salt thereof according to any one of Items 1 to 6, wherein $R^1$ represents a hydrogen atom, an acetyl group, or a propionyl group, $R^2$ represents an ethoxymethyl group, X represents a carbon atom, and Y represents a chlorine atom.

Item 8. A medicament comprising the 5-fluorouracil derivative or a salt thereof of any one of Items 1 to 7 as an active ingredient.

Item 9. An antitumor agent comprising the 5-fluorouracil derivative or a salt thereof of any one of Items 1 to 7 as an active ingredient.

Item 10. The antitumor agent according to Item 9, wherein the antitumor agent is used for treating at least one cancer selected from the group consisting of head and neck cancers, esophageal cancers, gastric cancers, colonic cancers, rectal cancers, liver cancers, gallbladder and bile duct cancers, biliary tract cancers, pancreatic cancers, lung cancers, breast cancers, ovarian cancers, cervical cancers, endometrial cancers, renal cancers, bladder cancers, prostatic cancers, testicular tumors, bone and soft tissue sarcoma, leukemia, malignant lymphomas, multiple myelomas, skin cancers, brain tumors, and mesotheliomas.

Item 11. A method for treating a cancer comprising administering an effective amount of the 5-fluorouracil derivative or a salt thereof of any one of Items 1 to 7 to a cancer patient.

Item 12. Use of the 5-fluorouracil derivative or a salt thereof of any one of Items 1 to 7 in the manufacture of an antitumor agent.

Advantageous Effects of Invention

Compound (I) of the present invention or a salt thereof exhibits excellent antitumor effects with reduced side effects such as gastrointestinal damage; therefore, it is useful as an antitumor agent. Furthermore, Compound (I) of the present invention or a salt thereof is also useful as an antitumor agent in terms of suppressing a reduction in the white blood cell count and the platelet count. Conventional 5-FU derivatives have a drawback in that their use results in a considerable reduction in the platelet count, particularly when they are used in combination with another antitumor agent. Accordingly, Compound (I) of the present invention or a salt thereof, with its reduced side effects, is useful as an antitumor agent.

Examples of diseases that can be treated by administering a drug comprising the compound of the present invention include, in the case of malignant tumors, head and neck cancers, esophageal cancers, gastric cancers, colonic cancers, rectal cancers, liver cancers, gallbladder and bile duct cancers, biliary tract cancers, pancreatic cancers, lung cancers, breast cancers, ovarian cancers, cervical cancers, endometrial cancers, renal cancers, bladder cancers, prostatic cancers, testicular tumors, bone and soft tissue sarcoma, leukemia, malignant lymphomas, multiple myelomas, skin cancers, brain tumors, and mesotheliomas. Among these, the compound of the present invention is particularly effective in treating gastric cancers, colonic cancers, rectal cancers, head and neck cancers, lung cancers, breast cancers, pancreatic cancers, biliary tract cancers, and the like.

BRIEF DESCRIPTION OF DRAWINGS

FIG. 1-1 shows the results of the antitumor effects of S-1 and Compound I-11 and changes in the body weight of rats in Test Example 7. FIG. 1-2 shows the results of the white blood cell count and the platelet count after administration of S-1 and Compound I-11 in Test Example 7.

[FIG. 2] FIG. 2-1 shows the results of the antitumor effects of S-1 and Compound I-10 and changes in the body weight of rats in Test Example 8. FIG. 2-2 shows the results of the white blood cell count and the platelet count after administration of S-1 and Compound I-10 in Test Example 8.

DESCRIPTION OF EMBODIMENTS

Figure 1:
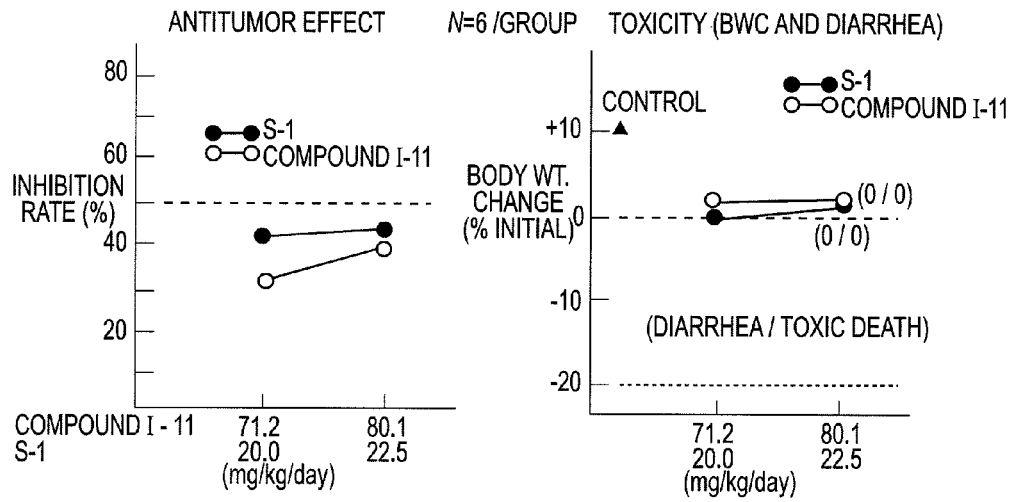
[FIG. 1]

The present invention relates to the 5-fluorouracil derivative represented by Formula (I) below or a salt thereof:

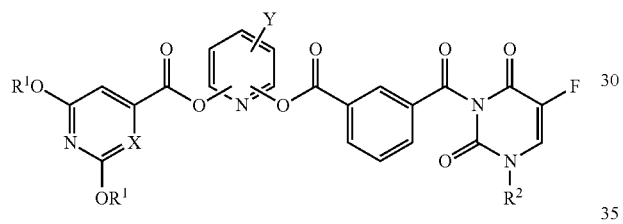
(I)

wherein $R^1$ represents a hydrogen atom or a protecting group of a hydroxy group, $R^2$ represents a lower alkoxy-lower alkyl group or a tetrahydrofuranyl group, X represents a carbon atom or a nitrogen atom, and Y represents a halogen atom or a cyano group.

In the present invention, the 5-fluorouracil derivative represented by Formula (I) above or a salt thereof includes their tautomers.

More specifically, the present invention includes the 5-fluorouracil derivative represented by Formula (I) or a salt thereof, wherein the group represented by the following formula:

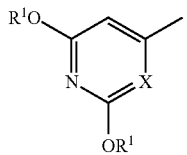

is a group represented by:

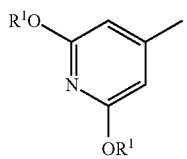

wherein $R^1$ represents a hydrogen atom or a protecting group of a hydroxy group;
a group represented by:

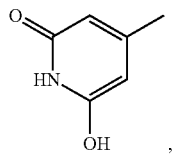

a group represented by:

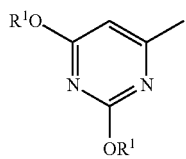

wherein $R^1$ represents a hydrogen atom or a protecting group of a hydroxy group; or
a group represented by:

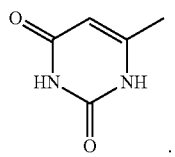

Specific examples of the groups represented by Formula (I) are as follows.

In Formula (I), $R^1$ represents a hydrogen atom or a protecting group of a hydroxy group.

The protecting group of a hydroxy group represented by $R^1$ may be any protecting group as long as it can be cleaved by a chemical procedure, such as hydrogenolysis, hydrolysis, electrolysis, and photolysis, or a biological process, such as performing hydrolysis in a human body. Specific examples thereof include acyl groups, such as substituted or unsubstituted aliphatic acyl groups and substituted or unsubstituted aromatic acyl groups or alicyclic acyl groups; lower alkoxycarbonyl groups; lower alkylcarbamoyl groups; substituted or unsubstituted lower alkyl groups; lower alkenyl groups; substituted or unsubstituted arylalkyl groups; silyl protecting groups; and amino acid residues.

Examples of aliphatic acyl groups include a formyl group, an acetyl group, a propionyl group, a butyryl group, an isobutyryl group, a pentanoyl group, an isovaleryl group, a pivaloyl group, a hexanoyl group and like $C_{1-6}$ linear or branched acyl groups. Examples of aromatic acyl groups include a benzoyl group, an α-naphthoyl group, and a β-naphthoyl group. These groups may have 1 to 3 substituents selected from a lower alkyl group, a lower alkoxy group, a halogen atom, a nitro group, a carboxy group, and the like.

Examples of alicyclic acyl groups include a cyclobutane carbonyl group, a cyclopentane carbonyl group, a cyclohexane carbonyl group, and like $C_{3-6}$ cycloalkyl carbonyl groups.

Examples of lower alkoxycarbonyl groups include a methoxycarbonyl group, an ethoxycarbonyl group, an n-propoxycarbonyl group, an isopropoxycarbonyl group, an n-butoxycarbonyl group, an isobutoxycarbonyl group, a secbutoxycarbonyl group, a tert-butoxycarbonyl group, a pentyloxy carbonyl group, a hexyloxycarbonyl group, and like $C_{2-7}$ linear or branched alkoxycarbonyl groups.

Examples of lower alkylcarbamoyl groups include a methylcarbamoyl group, an ethylcarbamoyl group, a propylcarbamoyl group, a butylcarbamoyl group, a pentylcarbamoyl group, a hexylcarbamoyl group, a dimethylcarbamoyl group, a diethylcarbamoyl group, and like carbamoyl groups mono- or di-substituted by a $C_{1-6}$ lower alkyl group.

Examples of lower alkyl groups include a methyl group, an ethyl group, an n-propyl group, an isopropyl group, an n-butyl group, an isobutyl group, a sec-butyl group, a tert-butyl group, an n-pentyl group, an isopentyl group, an n-hexyl group, an isohexyl group, and like $C_{1-6}$ linear or branched alkyl groups. These groups may have 1 to 3 substituents such as a halogen atom, and a lower alkoxy group. Specific examples thereof also include a chloromethyl group, a methoxymethyl group, an ethoxymethyl group, a methoxyethyl group, an ethoxyethyl group, and like substituted alkyl groups.

Examples of lower alkenyl groups include an ethenyl group, an allyl group, a butenyl group, a butadienyl group, a hexatrienyl group, and like $C_{2-6}$ linear or branched alkenyl groups.

Examples of arylalkyl groups include a benzyl group, a benzhydryl group, and a trityl group. These groups may have 1 to 5 or preferably 1 to 3 substituents such as a lower alkyl group, a lower alkoxy group, a halogen atom, and a nitro group.

Examples of silyl protecting groups include a trimethylsilyl group, a tert-butyldimethylsilyl group, a methyldiisopropylsilyl group, a triisopropylsilyl group, a tetraisopropyldisiloxyl group (TIPDS) group, and a diphenylmethylsilyl group.

Examples of amino acid residues include those formed by removing a hydroxy group from a carboxy group of an amino acid. These amino acid residues may be derived from natural or synthetic amino acid. Specific examples of usable amino acids include glycine, alanine, β-alanine, valine, and isoleucine; and any amino acid residues disclosed in Japanese Unexamined Patent Publication No. H1-104093 can be used.

Examples of lower alkyl groups usable as a substituent here include those listed above.

Examples of lower alkoxy groups include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an n-hexyloxy group, and like $C_{1-6}$ linear or branched alkoxy groups.

Examples of halogen atoms include a fluorine atom, a chlorine atom, a bromine atom, and an iodine atom.

$R^2$ represents a lower alkoxy-lower alkyl group or a tetrahydrofuranyl group.

In Formula (I), examples of the "lower alkoxy" moiety in a "lower alkoxy-lower alkyl group" represented by $R^2$ include a methoxy group, an ethoxy group, an n-propyloxy group, an isopropyloxy group, an n-butyloxy group, a sec-butyloxy group, a tert-butyloxy group, an n-pentyloxy group, an n-hexyloxy group, and like $C_{1-6}$ linear or branched alkoxy groups. Examples of the lower alkoxy moieties include preferably a $C_{1-3}$ alkoxy group, more preferably a methoxy group and ethoxy group, and still more preferably an ethoxy group. Examples of the "lower alkyl group" in the "lower alkoxy-lower alkyl group" include a methyl group, an ethyl group, an n-propyl group, an isopropyl group, an n-butyl group, an isobutyl group, a sec-butyl group, a tert-butyl group, an n-pentyl group, an isopentyl group, an n-hexyl group, an isohexyl group, and like $C_{1-6}$ linear or branched alkyl groups. Examples of the lower alkyl moieties include preferably a $C_{1-3}$ alkyl group, more preferably a methyl group and ethyl group, and still more preferably a methyl group.

Examples of "lower alkoxy-lower alkyl groups" include the aforementioned lower alkyl groups having the "lower alkoxy moieties" described above. Specific examples thereof include alkoxyalkyl groups such as a methoxymethyl group, an ethoxymethyl group, a propoxymethyl group, a methoxyethyl group, an ethoxyethyl group, a propoxyethyl group, a 3-methoxypropyl group, a 4-ethoxybutyl group, a 6-propoxyhexyl group, a 5-isopropoxypentyl group, a 1,1-dimethyl-2-butoxyethyl group, a 2-methyl-3-t-butoxypropyl group, a 2-pentyloxyethyl group, and a 2-hexyloxyethyl group. The lower alkoxy-lower alkyl group is preferably a methoxymethyl group, an ethoxymethyl group, or a propoxymethyl group, and more preferably an ethoxymethyl group.

Examples of tetrahydrofuranyl groups include a 2-tetrahydrofuranyl group and a 3-tetrahydrofuranyl group. Among these, a 2-tetrahydrofuranyl group is preferable.

X represents a carbon atom or a nitrogen atom.

Y represents a halogen atom or a cyano group. In Formula (I), examples of halogen atoms represented by Y include a fluorine atom, a chlorine atom, a bromine atom, and an iodine atom.

Examples of groups in a particularly preferable embodiment are as described below:

Preferably $R^1$ is a hydrogen atom, an allyl group, a benzyl group, an aliphatic acyl group, an aromatic acyl group, or an alicyclic acyl group, more preferably a hydrogen atom, a benzyl group, an acetyl group, a propionyl group, an isobutyryl group, a pivaloyl group, a benzoyl group, a p-chlorobenzoyl group, or a cyclopentane carbonyl group, and still more preferably a hydrogen atom, an acetyl group or a propionyl group.

Preferably $R^2$ is a lower alkoxymethyl group in which the lower alkoxy moiety has 1 to 6 carbon atoms or a 2-tetrahydrofuranyl group, more preferably a lower alkoxymethyl group in which the lower alkoxy moiety has 1 to 6 carbon atoms, and still more preferably an ethoxymethyl group.

Preferably X is a carbon atom.

Preferably Y is a fluorine atom or a chlorine atom, and more preferably a chlorine atom.

The preferable embodiments of $R^1$, $R^2$, X, and Y may be used in any combination.

The 5-fluorouracil derivative represented by Formula (I) of the present invention encompasses stereoisomers, optical isomers, solvates such as a hydrate, and crystalline polymorphisms.

The 5-fluorouracil derivative represented by Formula (I) of the present invention may be a salt. As such, a pharmacologically acceptable salt is preferable. Examples thereof include salts with an inorganic acid and salts with an organic acid.

Specific examples thereof include salts with an inorganic acid include hydrochloric acid, sulfuric acid, hydrobromic acid, hydroiodic acid, nitric acid, and phosphoric acid.

Specific examples thereof include salts with an organic acid include formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid, and methanesulfonic acid.

The compound of the present invention can be produced by various methods, and an example of such a method is illustrated by the scheme shown below. The materials necessary for synthesizing the compound of the present invention can be readily obtained from commercially available products or according to a production method disclosed in an article or the like. The substituents in Formula (I) are the same as those defined above.

Scheme 1

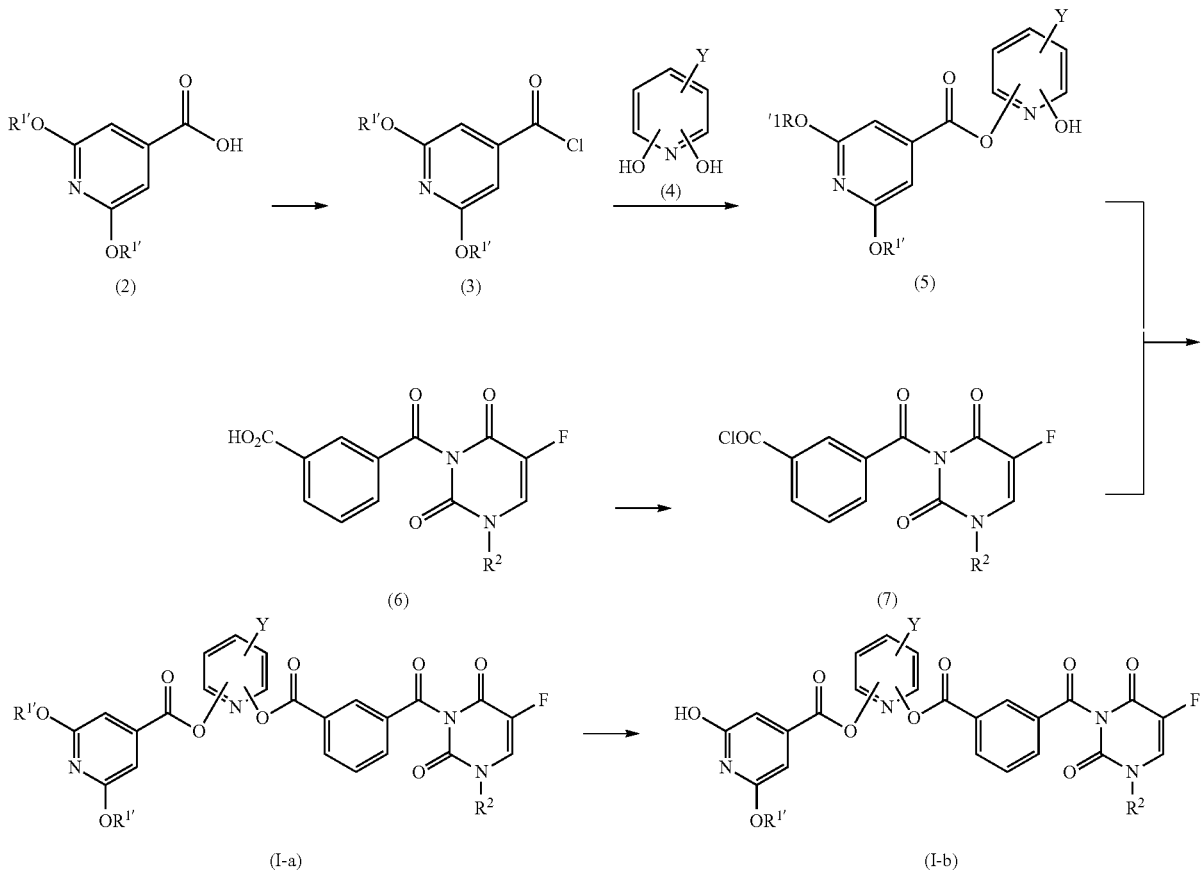

wherein R¹' represents an allyl group, or a substituted or unsubstituted benzyl group, R² represents a lower alkoxy-lower alkyl group or a tetrahydrofuranyl group, and Y represents a halogen atom or a cyano group.

Synthesis of Isonicotinic Acid Derivative (2)

A sodium or potassium salt of allyl alcohol, benzyl alcohol, or substituted benzyl alcohol is dissolved in a solvent that does not affect the reaction, such as tetrahydrofuran, toluene, and dimethylformamide, and preferably dimethylformamide. A sodium salt of 2,6-dichloroisonicotinic acid is added to the resulting solution at room temperature. The resulting mixture is stirred at 60 to 100° C. for 2 to 24 hours. The mixture is allowed to react, preferably, at 80° C. for 4 hours. Here, 2 to 10 equivalent, and preferably 4 equivalent amount of alcoholate is used relative to a sodium salt of 2,6-dichloroisonicotinic acid. After the reaction has completed, water is added to the reaction product, and a water layer is separated using ethyl acetate or a like solvent. The pH of the water layer is adjusted to 5 to 6 using 1N-hydrochloric acid or acetic acid. The result is subjected to extraction using ethyl acetate, a mixed solvent of ethyl acetate and n-hexane, toluene, or the like. The extract is dried over sodium sulfate, magnesium sulfate, etc., and then concentrated to obtain an isonicotinic acid derivative of allyloxy, benzyloxy, or substituted benzyloxy (2)(in the present specification, the isonicotinic acid derivative of allyloxy, benzyloxy, or substituted benzyloxy (2) may be referred to as isonicotinic acid derivative (2)).

Step 1 Synthesis of Isonicotinic Acid-Acid Chloride Derivative (3)

The isonicotinic acid derivative (2) obtained above is dissolved in a solvent that does not affect the reaction, such as chloroform, 1,2-dichloroethane, and toluene, and preferably toluene. Thereafter, thionyl chloride is added dropwise at room temperature to the solution thus prepared. The amount of the thionyl chloride used is 1 to 10 equivalent, and preferably 5 equivalent relative to the solution. After the dropwise addition has completed, the resulting mixture is stirred under reflux for 2 to 8 hours, and preferably for 4 hours. After the reaction has completed, the mixture is concentrated and the residue is used in the following step as is.

Synthesis of Pyridine Derivative (4)

The pyridine derivative (4) can be produced by a method disclosed in Japanese Unexamined Patent Publication No. H05-80451, Heterocycles, Vol. 36, No. 1, 145-148, 1993, etc.
These pyridine derivatives (4) are present as tautomers of a hydroxypyridine structure and a 2(1H)-pyridone structure.

Step 2 Synthesis of Ester Bonded Substance (5)

The pyridine derivative (4) obtained above is dissolved in an organic amine salt such as triethylamine, diisopropylethylamine, and dimethylaniline, preferably a mixture of triethylamine with a solvent that does not affect the reaction, such as dichloromethane, acetonitrile, dimethylformamide, dimethylacetamide, and preferably a mixture of triethylamine with dimethylacetamide. A dimethylacetamide solution of the isonicotinic acid-acid chloride derivative (3) obtained in Step 1 is added dropwise to the resulting substance under ice cooling. Here, 1.0 to 1.2 equivalent isonicotinic acid-acid chloride derivative (3) and 1.0 to 1.2 equivalent organic amine salt are used per pyridine derivative (4). After allowing the mixture to react at room temperature for 1 to 4 hours, water is added to the mixture, followed by extraction using ethyl acetate, a mixed solvent of ethyl acetate and n-hexane, toluene, or the like. The extract is dried over sodium sulfate, magnesium sulfate or the like, concentrated to recrystallization, purified by column chromatography, and then supplied to the following step.

Synthesis of Isophthalic Acid 5-Fluorouracil Monoamide (6)

The isophthalic acid 5-fluorouracil monoamide (6) can be produced by the method disclosed in Japanese Unexamined Patent Publication No. H02-164871.

Step 3 Synthesis of Isophthalic Acid 5-Fluorouracil Monoamide-Acid Chloride (7)

The isophthalic acid 5-fluorouracil monoamide (6) is dissolved in a solvent that does not affect the reaction, such as dichloromethane, chloroform, 1,2-dichloroethane, and toluene, and preferably dichloromethane. Thionyl chloride is added dropwise to the resulting solution at room temperature. The amount of thionyl chloride is 1 to 4 equivalent, and preferably 1.2 equivalent relative to the solution. After the dropwise addition has completed, the resulting mixture is stirred under reflux for 2 to 8 hours, and preferably 4 hours. After the reaction has completed, the mixture is concentrated and the residue is supplied to the following step as is.

Step 4 Synthesis of Compound of the Present Invention (I-a)

The ester bonded substance (5) obtained in Step 2 is dissolved in an organic amine salt such as triethylamine, diisopropylethylamine, and dimethylaniline, and preferably triethylamine and a solvent that does not affect the reaction, such as dichloromethane, acetonitrile, and dimethylformamide. To the solution thus obtained, a dichloromethane solution of the isophthalic acid 5-fluorouracil monoamide-acid chloride (7) obtained in Step 3 is added dropwise under ice cooling. Here, 1.0 to 1.2 equivalent isophthalic acid 5-fluorouracil monoamide-acid chloride (7) and 1.0 to 1.2 equivalent organic amine salt are used relative to the ester bonded substance (5). After allowing the mixture to react at room temperature for 1 to 4 hours, water is added to the reaction product, followed by extraction using dichloromethane or the like. The extract is dried over sodium sulfate, magnesium sulfate or the like, concentrated to recrystallization, purified by column chromatography, and then supplied to the following step.

Step 5 Synthesis of Compound of the Present Invention (I-b)

Deprotection is performed according to the method disclosed in Green's "Protective Group in Organic Synthesis".

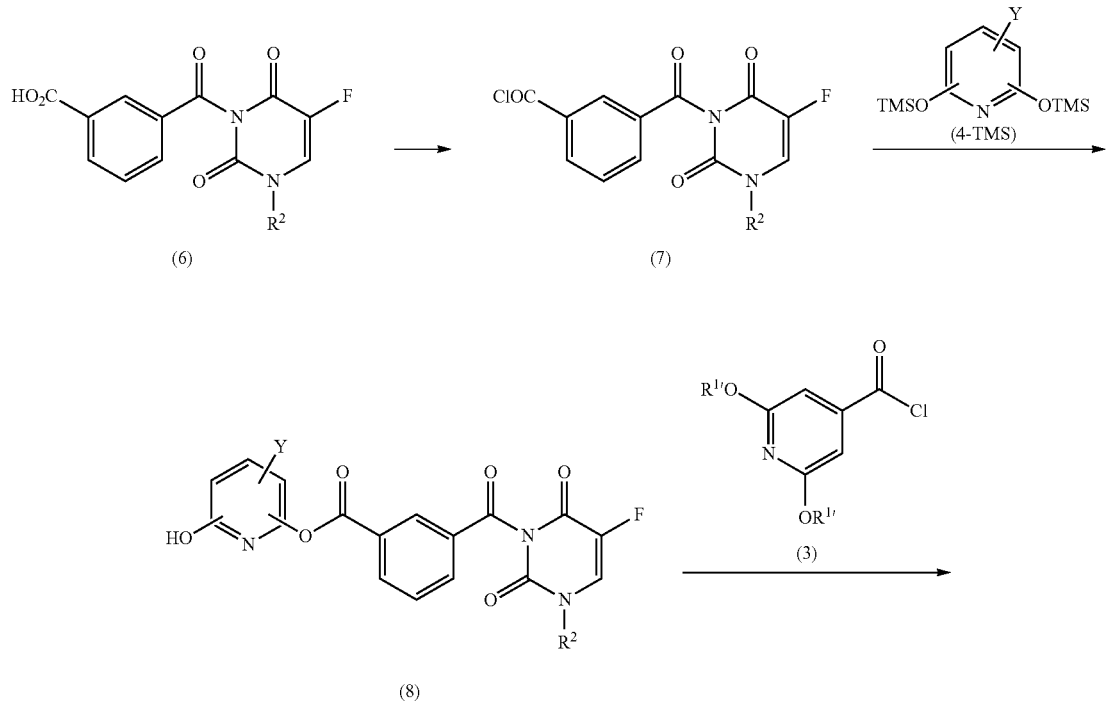

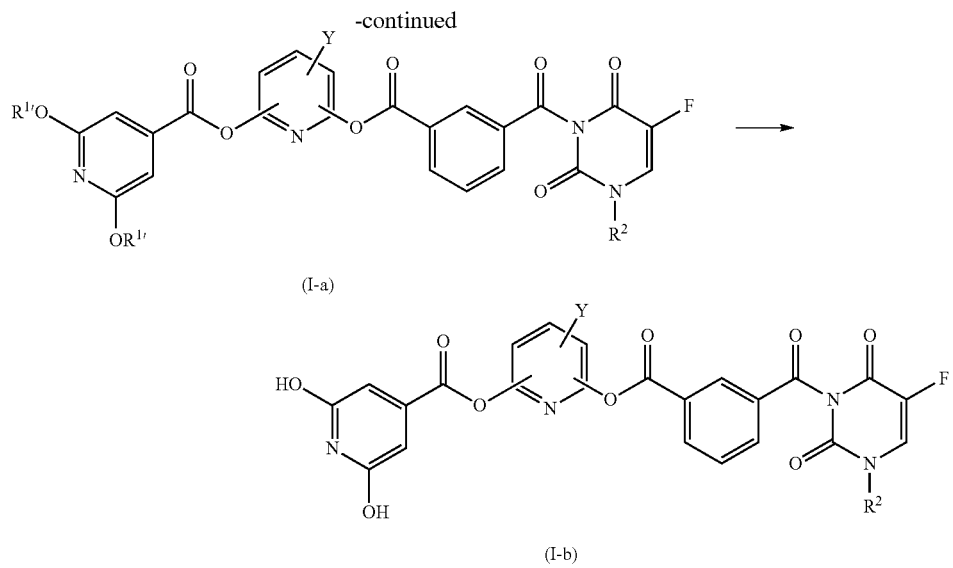

(I-a)

(I-b)

wherein $R^{1'}$, $R^2$, and Y are the same as defined above.

Step 6 Synthesis of Isophthalic Acid Monoamide-Monoester (8)

A pyridine derivative (4-TMS) that was trimethylsilylated (TMS) according to the method disclosed in Chem. Pharm. Bull. Vol. 41, No. 9, 1498-1506, 1993 is dissolved in a solvent that does not affect the reaction, such as dichloromethane, acetonitrile, and dimethylformamide, and preferably acetonitrile. To the solution thus obtained, an acetonitrile solution of isophthalic acid 5-fluorouracil monoamide-acid chloride (7) is added dropwise under ice cooling. Subsequently, Lewis acid, such as stannic chloride and titanium tetrachloride, is added thereto dropwise. Here, 0.8 to 1.0 equivalent isophthalic acid 5-fluorouracil monoamide-acid chloride (7) and catalytic amount of Lewis acid are used relative to pyridine derivative (4-TMS). After allowing the mixture to react at room temperature for 1 to 4 hours, water is added to the reaction liquid, followed by extraction using dichloromethane or the like. The extract is dried over sodium sulfate, magnesium sulfate or the like, concentrated to recrystallization, purified by column chromatography, and then supplied to the following step.

Step 7 Synthesis of Compound of the Present Invention (I-a)

The isophthalic acid monoamide-monoester (8) is dissolved in a mixture of an organic amine salt such as triethylamine, diisopropylethylamine, and dimethylaniline, preferably triethylamine and a solvent that does not affect the reaction, such as dichloromethane, acetonitrile, and dimethylformamide, and preferably dichloromethane. A dichloromethane solution of isonicotinic acid-acid chloride derivative (3) is added dropwise to the resulting mixture. Here, 1.0 to 1.2 equivalent isonicotinic acid-acid chloride derivative (3) and 1.0 to 1.2 equivalent organic amine salt are used relative to the isophthalic acid monoamide-monoester (8). After allowing the mixture to react at room temperature for 1 to 4 hours, water is added to the reaction liquid, followed by extraction using dichloromethane or the like. The extract is dried over sodium sulfate, magnesium sulfate or the like, concentrated to recrystallization, purified by column chromatography, and then supplied to Step 5 shown in Scheme 1.

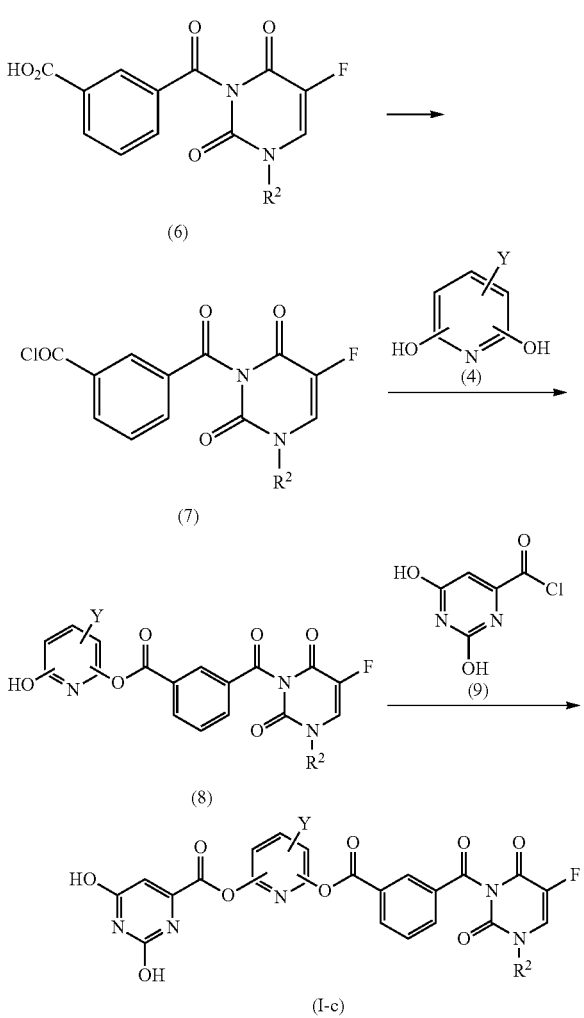

Scheme 3 wherein $R^2$ and Y are as defined above.

Synthesis of Orotic Acid-Acid Chloride (9)

Thionyl chloride is added dropwise to orotic acid at room temperature, together with a solvent that does not affect the reaction, such as chloroform, 1,2-dichloroethane, and toluene, or without solvent. Here, 1 to 5 equivalent, preferably 4 equivalent thionyl chloride is used relative to orotic acid. After the dropwise addition has completed, the resulting mixture is stirred under reflux for 2 to 8 hours, and preferably for 4 hours. After the reaction has completed, the mixture is concentrated and the residue is supplied to the following step as is.

Step 8 Synthesis of Compound of the Present Invention (I-c)

The isophthalic acid monoamide-monoester (8) is dissolved in a mixed liquid of an organic amine salt such as triethylamine, diisopropylethylamine, and dimethylaniline, preferably triethylamine with a solvent that does not affect the reaction, such as dichloromethane, acetonitrile, and dimethylformamide, and preferably a mixed liquid of triethylamine with dichloromethane. A dichloromethane solution of orotic acid-acid chloride (9) is added dropwise to the resulting solution under ice cooling. Here, 1.0 to 1.2 equivalent orotic acid-acid chloride (9) and 1.0 to 1.2 equivalent organic amine salt are used relative to the isophthalic acid monoamide-monoester (8). After allowing the mixture to react at room temperature for 1 to 4 hours, water is added to the reaction product, followed by extraction using dichloromethane or the like. The extract is dried over sodium sulfate, magnesium sulfate or the like, concentrated to recrystallization, and then purified by column chromatography.

dissolved in a solvent that does not affect the reaction, such as dimethoxyethane, dichloromethane, acetonitrile, dimethylformamide, and dimethylacetamide, and preferably dimethoxyethane. An organic amine salt, such as pyridine, triethylamine, diisopropylethylamine, and dimethylaniline, and preferably pyridine, is added to the resulting solution under ice cooling. Here, 2.2 to 4.0 equivalent acid chloride and 2.2 to 4.0 equivalent organic amine salt are used relative to pyridine derivative (I-d). After allowing the mixture to react under ice cooling for 0.5 to 4 hours, water is added to the reaction liquid, followed by extraction using ethyl acetate, a mixed solvent of ethyl acetate and n-hexane, toluene, or the like. The extract is dried over sodium sulfate, magnesium sulfate, etc., concentrated to recrystallization, and then purified by column chromatography, etc.

As described above, Compound (I) of the present invention and salts thereof exhibit an excellent antitumor effect with reduced side effects such as gastrointestinal damage; therefore, they are useful as an antitumor agent. Accordingly, Compound (I) of the present invention and salts thereof are effective in treating cancers. In the present invention, cancer treatments include the administration of Compound (I) of the present invention or a salt thereof in order to prevent the recurrence of cancer after treating the cancer by radiation, surgical operation, etc.

When Compound (I) of the present invention or a salt thereof is used for treating the aforementioned diseases of mammals, including humans, the dosage, number of administrations, and the like should vary depending on the conditions and severity of the targeted disease, and the administration route of Compound (I) of the present invention. The dosage, number of administrations, and the like also vary depending on the age, body weight, general health condition,

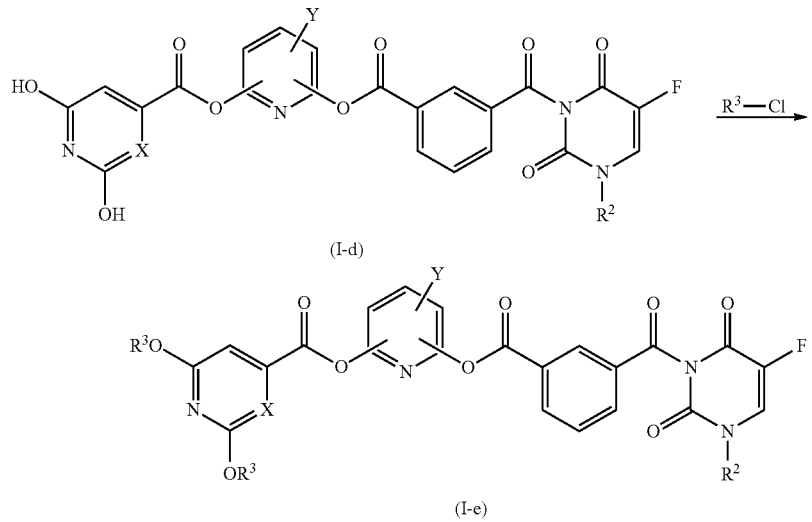

Scheme 4 wherein X represents a carbon atom or a nitrogen atom, $R^3$ represents a protecting group of a hydroxy group, and $R^2$ and Y are the same as defined above.

Step 9 Synthesis of Compound of the Present Invention (I-E) Wherein $R^1$ is Protecting Group of Hydroxy Group The pyridine derivative (I-d) obtained through Schemes 2 and 3 and an acid chloride represented by Formula $R^3$—Cl are sex, diet, administration time, excretion speed, concomitant drug, response, and the like of the patient. Compound (I) of the present invention and salts thereof are usually orally or parenterally administered. The dosage is generally a therapeutically effective amount for treating the aforementioned diseases, i.e., about 0.001 to 100 mg, and preferably about 0.01 to 50 mg/kg per day per kg of body weight of the mammal, such as a human. However, a dosage outside the above range may be applied depending on the case.

By blending an effective amount of the compound of the present invention with physiologically acceptable carriers, the compound of the present invention can be administered orally or parenterally (e.g., external use, inhalation, subcutaneous injection, arterial and intravenous injection, intramuscular injection, intravesical instillation, intracerebral instillation, rhinenchysis, and eye drops) as solid preparations such as a tablet, capsule, granule, and powder; liquid preparations such as a syrup and injection; and as external preparations such as an ointment, lotion, gel, and cream.

Various conventional organic or inorganic carriers usable as preparation materials are used as pharmacologically acceptable carriers in the present invention. Specific examples thereof include excipients, lubricants, binders, and disintegrants used in solid preparations; and solvents, solubilizers, suspending agents, tonicity adjusting agents, buffers, and soothing agents used in liquid preparations. Preparation additives such as antiseptics, antioxidants, colorants, and sweeteners may be used if necessary. Preferable examples of excipients include lactose, D-mannitol, starch, crystalline cellulose, and light anhydrous silicic acid. Preferable examples of lubricants include magnesium stearate, calcium stearate, talc, and colloidal silica. Preferable examples of binders include crystalline cellulose, white sugar, D-mannitol, dextrin, hydroxypropylcellulose, hydroxypropylmethylcellulose, and polyvinyl pyrrolidone. Preferable examples of disintegrants include starch, carboxymethylcellulose, carboxymethyl cellulose calcium, croscarmellose sodium, and sodium carboxymethyl starch. Preferable examples of solvents include water for injection, alcohol, propylene glycol, macrogol, sesame oil, and corn oil. Preferable examples of solubilizers include polyethylene glycol, propylene glycol, D-mannitol, benzyl benzoate, ethanol, trisaminomethane, cholesterol, triethanolamine, sodium carbonate, and sodium citrate. Preferable examples of suspending agents include surfactants such as stearyltriethanolamine, sodium lauryl sulfate, lauryl aminopropionic acid, lecithin, benzalkonium chloride, benzethonium chloride, and glycerol monostearate; and hydrophilic polymers such as polyvinyl alcohol, polyvinyl pyrrolidone, sodium carboxymethylcellulose, methylcellulose, hydroxymethylcellulose, hydroxyethylcellulose, and hydroxypropylcellulose. Preferable examples of buffers include buffer solutions of phosphate, acetate, carbonate, and citrate. Preferable examples of soothing agents include benzyl alcohol. Preferable examples of antiseptics include esters of parahydroxybenzoic acid, chlorobutanol, benzyl alcohol, phenethyl alcohol, dehydroacetic acids, and sorbic acids. Preferable examples of antioxidants include sulfite salts and ascorbic acid salts.

EXAMPLES

Hereinbelow, the present invention is specifically described with reference to Comparative Examples, Examples, and Test Examples. However, the present invention is not limited to these specific embodiments.

Reference Example 1

Synthesis of 2,6-dibenzyloxyisonicotinic acid (Compound 2a)

In an argon atmosphere, 2,6-dichloroisonicotinic acid (57.6 g) was gradually added to 55% sodium hydride (52.5 g) and dimethylformamide (1 L) while being cooled and stirred. Subsequently, benzyl alcohol (93 mL) was gradually added dropwise to the reaction product at the same temperature. After hydrogen was no longer generated, the reaction product was stirred for 4 hours at 80° C., and water (1 L) was then added thereto. The mixture was separated by a mixed solvent (1 L) of ethyl acetate and n-hexane (1:1). The acidity of the aqueous layer was lowered with acetic acid (75.5 mL), and water (1.7 L) was further added thereto. The precipitate was filtered and dried to obtain Compound 2a.

Yield: 77.17 g (77%)

$^1$H-NMR (DMSOd$_6$, δPPM):

13.60 (1H, brs), 7.43-7.29 (10H, m) 6.81 (2H, s), 5.36 (4H, s)

Melting point: 145-147° C.

Reference Example 2

Synthesis of 2,6-di-p-methoxybenzyloxyisonicotinic acid (Compound 2b)

Compound 2b was synthesized according to the method of Reference Example 1, except that p-methoxybenzyl alcohol was used instead of benzyl alcohol.

$^1$H-NMR (DMSOd$_6$, δPPM):

13.56 (1H, brs), 7.39 (4H, d, J=8.4 Hz), 6.95 (4H, d, J=8.6 Hz), 5.33 (4H, s), 3.77 (6H, s)

Reference Example 3

Synthesis of 2,6-diallyloxyisonicotinic acid (Compound 2c)

Compound 2c was synthesized according to the method of Reference Example 1, except that allyl alcohol was used instead of benzyl alcohol.

$^1$H-NMR (DMSOd$_6$, δPPM):

13.60 (1H, brs), 6.77 (2H, s), 6.15-5.99 (2H, m), 5.38 (2H, dd, J=17.2 Hz, J=1.5 Hz), 5.23 (2H, d, J=10.4 Hz), 4.82 (4H, d, J=5.4 Hz)

Reference Example 4

Synthesis of 4-{2,6-dibenzyloxyisonicotinoyloxy}-5-chloro-2-hydroxypyridine (Compound 5a), 2-{2,6-dibenzyloxyisonicotinoyloxy}-5-chloro-4-hydroxypyridine (Compound 5b), and 2,4-di{2,6-dibenzyloxyisonicotinoyloxy}-5-chloropyridine (Compound 5c)

Thionyl chloride (98.5 mL) and dimethylformamide (1.7 mL) were added dropwise to a solution of 2,6-dibenzyloxyisonicotinic acid (Compound 2a) (75.45 g) obtained in Reference Example 1 and toluene (800 mL), and the mixture was stirred at 80° C. for 4.5 hours. After being cooled, the solvents were evaporated. Without purification, the residual acid chloride was dissolved in dimethylacetamide (100 mL) to obtain a dimethylacetamide solution of acid chloride to be used in the following reaction. The dimethylacetamide solution of acid chloride was added dropwise under ice cooling to a solution of 2,4-dihydroxy-5-chloropyridine (31.9 g), triethylamine (31.19 mL) and dimethylacetamide (1.6 L). The resulting mixture was stirred at room temperature for 1 hour, and water (1.7 L) was then added thereto. The mixture was separated by a mixed solvent (1 L) of ethyl acetate and n-hexane (3:1). After the solution was dried with sodium sulfate, the solvent was evaporated. The precipitate was filtered and dried to obtain Compound 5a.

Yield: 44.8 g (45%)

Meanwhile, the filtrate was concentrated and the resulting residue was purified by silica gel column chromatography (eluted with ethyl acetate/n-hexane (1:1)) to obtain Compound 5b (18.94 g) and Compound 5c (4.74 g). Compound 5a
$^1$H-NMR (DMSOd$_6$, δPPM):
12.09 (1H, brs), 7.91 (1H, s), 7.50-7.30 (10H, m), 6.99 (2H, s), 6.58 (1H, s), 5.42 (4H, s)
Melting point: 149-150° C.
Compound 5b
$^1$H-NMR (DMSOd$_6$, δPPM):
12.26 (1H, brs), 8.27 (1H, s), 7.50-7.30 (10H, m), 6.98 (2H, s), 6.86 (1H, s), 5.42 (4H, s)
Melting point: 136-138° C. (decomposition temperature)
Compound 5c
$^1$H-NMR (DMSOd$_6$, δPPM):
8.75 (1H, s), 7.79 (1H, s), 7.50-7.30 (20H, m), 7.05 (2H, s), 7.02 (2H, s), 5.42 (8H, s)

Reference Example 5

Synthesis of 2,6-dihydroxy-3-fluoropyridine (Compound 4a)

2,6-Dibenzyloxy 5-fluoronicotinic acid (13.30 g) was obtained using 2,6-dichloro-5-fluoronicotinic acid (15.15 g) as a starting compound, by the same method as in Reference Example 1.
$^1$H-NMR (DMSOd$_6$, δPPM):
8.02 (1H, d, J=10.2 Hz), 7.49-7.28 (10H, m), 5.48 (2H, s), 5.45 (2H, s)
Next, 2,6-dibenzyloxy-5-fluoronicotinic acid (5.00 g) was dissolved in dioxane (50 mL), and 20% palladium hydroxide (50% wet, 500 mg) was added thereto and reacted under a hydrogen atmosphere for 1 hour. The palladium hydroxide was filtered through Celite from the resulting reaction product, and the solvent was evaporated to obtain a compound, i.e., 2,6-dihydroxy-5-fluoronicotinic acid (2.58 g).
Yield: 88%
$^1$H-NMR (DMSOd$_6$, δPPM):
7.44 (1H, d, J=11.4 Hz)
2,6-Dihydroxy-5-fluoronicotinic acid (2.25 g) was dissolved in dioxane (25 mL) and refluxed for 15 minutes. After being cooled, the solvent was evaporated to obtain Compound 4a (1.65 g). Yield: 99%$^1$ H-NMR (DMSOd$_6$, δPPM): 7.26 (1H, dd, J=7.7 Hz, J=11.0 Hz), 5.45 (1H, d, J=6.6 Hz)

Reference Example 6

6-{2,6-dibenzyloxyisonicotinoyloxy}-3-fluoro-2-hydroxypyridine (Compound 5d)

Compound 5d was synthesized according to the method of Reference Example 4, except that Compound 4a obtained in Reference Example 5 was used instead of 2,4-dihydroxy-5-chloropyridine.
$^1$H-NMR (DMSOd$_6$, δPPM):
7.79 (1H, t, J=9.0 Hz), 7.47-7.30 (11H, m), 6.98 (2H, s), 5.42 (4H, s)

Reference Example 7

Synthesis of 3-{3-[4-hydroxy-5-chloro-2-pyridyloxycarbonyl]benzoyl}-1-ethoxymethyl-5-fluorouracil (Compound 8a) and 3-{3-[2-hydroxy-5-chloro-4-pyridyloxycarbonyl]benzoyl}-1-ethoxymethyl-5-fluorouracil (Compound 8b)

1-Ethoxymethyl-3-m-hydroxycarbonylbenzoyl-5-fluorouracil (3.46 g) was dissolved in methylene chloride (50 mL). Thionyl chloride (0.9 mL) and dimethylformamide (0.04 mL) were then added thereto. The resulting reaction product was refluxed for 2 hours, and the solvents were then evaporated. The residue was dissolved in methylene chloride (12 mL) to obtain a methylene chloride solution of acid chloride. After 2,4-dihydroxy-5-chloropyridine (1.5 g) was fluxed in hexamethyldisilazane (15 mL) for 6 hours, the solvent was evaporated, and the resulting residue was dissolved in methylene chloride (30 mL). The above methylene chloride solution of acid chloride was added dropwise thereto under ice cooling, and anhydrous stannic chloride (0.15 mL) was subsequently added thereto. The mixture was stirred at room temperature for 15 hours. After being neutralized with triethylamine, the residue obtained by evaporating the solvents was purified by silica gel column chromatography (eluted with ethyl acetate/n-hexane (1:2)) to obtain Compound 8a (2.15 g; yield: 45%) and Compound 8b (496 mg; yield: 10%).
Compound 8a
$^1$H-NMR (DMSOd$_6$, δPPM):
8.63 (1H, t, J=1.6 Hz), 8.49 (2H, d, J=8.2 Hz), 8.45 (1H, d, J=6.7 Hz), 8.28 (1H, s), 7.86 (1H, t, J=7.8 Hz), 6.91 (1H, s), 5.11 (2H, s), 3.58 (2H, q, J=6.9 Hz), 1.11 (3H, t, J=7.0 Hz)
Compound 8b
$^1$H-NMR (DMSOd$_6$, δPPM):
8.65 (1H, t, J=3.3 Hz), 8.51 (2H, dt, J=1.7, 7.7 Hz), 8.46 (1H, d, J=6.6 Hz), 7.93 (1H, s), 7.89 (1H, t, J=7.8 Hz), 6.63 (1H, s), 5.11 (2H, s), 3.58 (2H, q, J=7.0 Hz), 1.12 (3H, t, J=7.1 Hz)

Reference Example 8

Alternative synthesis of 3-{3-[4-hydroxy-5-chloro-2-pyridyloxycarbonyl]benzoyl}-1-ethoxymethyl-5-fluorouracil (Compound 8a)

1-Ethoxymethyl-3-m-hydroxycarbonylbenzoyl-5-fluorouracil (3.46 g) was dissolved in methylene chloride (50 mL). Thionyl chloride (0.9 mL) and dimethylformamide (0.04 mL) were then added thereto. The resulting reaction product was refluxed for 2.5 hours, and the solvents were then evaporated. The residue was dissolved in dimethylacetamide (12 mL) to obtain a dimethylacetamide solution of acid chloride. The dimethylacetamide solution of acid chloride was added dropwise under ice cooling to a solution of 2,4-dihydroxy-5-chloropyridine (1.5 g), triethylamine (1.57 mL), and dimethylacetamide (15 mL). The resulting reaction product was stirred at room temperature for 8 hours. Water was added thereto, and the mixture was separated by a mixed solvent of ethyl acetate and n-hexane (1:1). The organic layer was dried with sodium sulfate, and the solvent was then evaporated. The residue was purified by silica gel column chromatography (eluted with ethyl acetate/n-hexane (1:1)) to obtain Compound 8a (668 mg). Yield: 14%

Reference Example 9

Alternative synthesis of 2-{2,6-dibenzyloxyisonicotinoyloxy}-5-chloro-4-hydroxypyridine (Compound 5b), 4-{2,6-dibenzyloxyisonicotinoyloxy}-5-chloro-2-hydroxypyridine (Compound 5a), and 2,4-di{2,6-dibenzyloxyisonicotinoyloxy}-5-chloropyridine (Compound 5c)

Acid chloride was obtained using Compound 2a (1 g) obtained in Reference Example 1 as a starting compound, by the same method as that used in Reference Example 8. Further, as is the case with Reference Example 7, 2,4-dihydroxy- 5-chloropyridine (1.0 g) was trimethylsilylated and then reacted with acid chloride. After being neutralized with triethylamine, the residue obtained by evaporating the solvent was purified by silica gel column chromatography (eluted with ethyl acetate/n-hexane (1:1)) to obtain Compound 5b (1.38 g; yield: 44%), Compound 5a (675 mg; yield: 21%), and Compound 5c (647 mg; yield: 12%).

Example 1

Synthesis of 3-{3-[4-(2,6-dibenzyloxyisonicotinoyloxy)-5-chloro-2-pyridyloxycarbonyl]benzoyl}-1-ethoxymethyl-5-fluorouracil (Compound I-1)

1-Ethoxymethyl-3-m-hydroxycarbonylbenzoyl-5-fluorouracil (17 g) was dissolved in methylene chloride (200 mL). Thionyl chloride (5.5 mL) and dimethylformamide (0.4 mL) were then added thereto. The resulting reaction product was refluxed for 2.5 hours, and the solvents were then evaporated. The residue was dissolved in methylene chloride (60 mL) to obtain a methylene chloride solution of acid chloride. This solution was added dropwise under ice cooling to a solution of Compound 5a (21.27 g) obtained in Reference Example 4, triethylamine (7.3 mL) and methylene chloride (180 mL). The resulting reaction product was stirred at room temperature for 1 hour, and the solvents were then evaporated. The resulting residue was purified by silica gel column chromatography (eluted with ethyl acetate/n-hexane (1:1)) to obtain Compound I-1 (25.5 g). Yield: 71%

$^1$H-NMR (DMSOd$_6$, δPPM):
8.77 (1H, s), 8.67 (1H, t, J=1.6 Hz), 8.54-8.50 (2H, m), 8.45 (1H, d, J=6.6 Hz), 7.88 (1H, t, J=7.9 Hz), 7.83 (1H, s), 7.50-7.30 (10H, m), 7.06 (2H, s), 5.43 (4H, s), 5.11 (2H, s), 3.58 (2H, q, J=7.0 Hz), 1.11 (3H, t, J=7.0 Hz)
Melting point: 66-69° C.

Example 2

Synthesis of 3-{3-[4-(2,6-dihydroxyisonicotinoyloxy)-5-chloro-2-pyridyloxycarbonyl]benzoyl}-1-ethoxymethyl-5-fluorouracil (Compound I-2)

Compound I-1 (25.3 g) obtained in Example 1 was dissolved in dioxane (800 mL), and 20% palladium hydroxide (50% wet, 2.53 g) was added thereto and reacted under a hydrogen atmosphere for 1 hour. The palladium hydroxide was filtered through Celite from the resulting reaction product and washed with acetone (200 mL). The filtrate (i.e., dioxane and the acetone solution) was concentrated, and the resulting residue was crystallized from acetone-n-hexane (1:1) to obtain Compound I-2 (13.14 g). Yield: 68%

$^1$H-NMR (DMSOd$_6$, δPPM):
11.57 (2H, brs), 8.77 (1H, s), 8.67 (1H, t, J=1.6 Hz), 8.55-8.49 (2H, m), 8.45 (1H, d, J=6.6 Hz), 7.89 (1H, t, J=7.9 Hz), 7.83 (1H, s), 6.47 (2H, brs), 5.12 (2H, s), 3.59 (2H, q, J=7.0 Hz), 1.12 (3H, t, J=7.0 Hz)
Melting point: 125-129° C.

Example 3

Synthesis of 3-{3-[2-(2,6-dibenzyloxyisonicotinoyloxy)-5-chloro-4-pyridyloxycarbonyl]benzoyl}-1-ethoxymethyl-5-fluorouracil (Compound I-3)

Compound I-3 was synthesized according to the method of Example 1, except that Compound 5b obtained in Reference Example 4 was used instead of Compound 5a.

$^1$H-NMR (DMSOd$_6$, δPPM):
8.77 (1H, s), 8.71 (1H, t, J=1.6 Hz), 8.58-8.53 (2H, m), 8.46 (1H, d, J=6.6 Hz), 7.91 (1H, t, J=7.9 Hz), 7.83 (1H, s), 7.50-7.30 (10H, m), 7.03 (2H, s), 5.43 (4H, s), 5.11 (2H, s), 3.58 (2H, q, J=7.0 Hz), 1.12 (3H, t, J=7.0 Hz)

Example 4

Synthesis of 3-{3-[2-(2,6-dihydroxyisonicotinoyloxy)-5-chloro-4-pyridyloxycarbonyl]benzoyl}-1-ethoxymethyl-5-fluorouracil (Compound I-4)

Compound I-4 was synthesized using Compound I-3 obtained in Example 3, according to the method of Example 2.

$^1$H-NMR (DMSOd$_6$, δPPM):
8.77 (1H, s), 8.71 (1H, brs), 8.57-8.53 (2H, m), 8.47 (1H, d, J=6.4 Hz), 7.92 (1H, t, J=7.9 Hz), 7.83 (1H, s), 6.41 (2H, brs), 5.12 (2H, s), 3.59 (2H, q, J=6.3 Hz), 1.12 (3H, t, J=7.1 Hz)

Example 5

Synthesis of 3-{3-[6-(2,6-dibenzyloxyisonicotinoyloxy)-3-fluoro-2-pyridyloxycarbonyl]benzoyl}-1-ethoxymethyl-5-fluorouracil (Compound I-5)

Compound I-5 was synthesized according to the method of Example 1, except that Compound 5d obtained Reference Example 6 was used instead of Compound 5a.

$^1$H-NMR (DMSOd$_6$, δPPM):
8.71 (1H, t, J=1.5 Hz), 8.57-8.53 (m, 2H), 8.44 (1H, d, J=6.6 Hz), 8.33 (1H, t, J=8.6 Hz), 7.90 (1H, t, J=7.9 Hz), 7.62 (1H, dd, J=2.7 Hz, J=8.7 Hz), 7.46-7.32 (10H, m), 5.42 (4H, s), 5.12 (2H, s), 3.58 (2H, q, J=7.0 Hz), 1.12 (3H, t, J=7.0 Hz)

Example 6

Synthesis of 3-{3-[6-(2,6-hydroroxyisonicotinoyloxy)-3-fluoro-2-pyridyloxycarbonyl]benzoyl}-1-ethoxymethyl-5-fluorouracil (Compound I-6)

Compound I-6 was synthesized using Compound I-5 obtained in Example 5, according to the method of Example 2.

$^1$H-NMR (DMSOd$_6$, δPPM):
8.71 (1H, t, J=1.6 Hz), 8.58-8.53 (2H, m), 8.44 (1H, d, J=6.8 Hz), 8.32 (1H, t, J=8.6 Hz), 7.91 (1H, t, J=7.8 Hz), 7.60 (1H, dd, J=2.8 Hz, J=8.6 Hz), 6.41 (2H, brs), 5.11 (2H, s), 3.58 (2H, q, J=7.0 Hz), 1.11 (3H, t, J=7.0 Hz)

Example 7

Synthesis of 3-{3-[4-(2,6-dibenzyloxy isonicotinoyloxy)-5-chloro-2-pyridyloxycarbonyl]benzoyl}-1-ethoxymethyl-5-fluorouracil (Compound I-1)

Thionyl chloride (0.23 mL) and dimethylformamide (0.01 mL) were added dropwise to a solution of Compound 2a (217 mg) obtained in Reference Example 1 and toluene (4 mL), and the mixture was stirred at 80° C. for 4.5 hours. After the resulting mixture was cooled, the solvents were evaporated. Without purification, the residual acid chloride was dissolved in dioxane (2 mL) to obtain a dioxane solution of acid chloride to be used in the following reaction. The dioxane solution of acid chloride was added dropwise under ice cooling to a solution of Compound 8a (100 mg) obtained in Reference Example 7 or Reference Example 8, triethylamine (0.01 mL)

and dioxane (10 mL). The resulting mixture was stirred at room temperature for 8 hours, and the solvents were then evaporated. The resulting residue was purified by silica gel column chromatography (eluted with ethyl acetate/n-hexane (1:1)) to obtain Compound I-1 (119 mg).
Yield: 92%.

Example 8

Synthesis of 3-{3-[2-(orotinoyloxy)-5-chloro-4-pyridyloxycarbonyl]benzoyl}-1-ethoxymethyl-5-fluorouracil (Compound I-7)

Thionyl chloride (35 mL) and pyridine (0.17 mL) were added to orotic acid (6 g) and the mixture was refluxed for 20 hours. Subsequently, thionyl chloride was evaporated from the resulting reaction product, and the residue was obtained as orotic acid acid chloride without purification. The resulting acid chloride (0.59 g) and Compound 8b (0.78 g) obtained in Reference Example 7 were dissolved in dioxane (10 mL). A solution of triethylamine (0.46 mL) and dioxane (5 mL) was then added to the above solution, and stirred at room temperature for 30 minutes. Unwanted materials were removed by filtration from the resulting reaction product, and the solvents were then evaporated. The solution was separated by ethyl acetate and purified water. The resulting residue was dried with magnesium sulfate, and the solvent was then evaporated. The resulting crude crystals were washed with a mixed solvent (10 mL) of n-hexane and ethyl acetate (3:1) to obtain Compound I-7 (859 mg; yield: 85%).
$^1$H-NMR (DMSOd$_6$, δPPM):
11.53 (1H, s), 11.49 (1H, s), 8.78 (1H, s), 8.71 (1H, s), 8.55 (2H, d, J=7.9 Hz), 8.47 (1H, d, J=6.6 Hz), 7.92 (1H, t, J=7.9 Hz), 7.82 (1H, s), 6.35 (1H, s), 5.11 (2H, s), 3.58 (2H, q, J=7.0 Hz), 1.12 (3H, t, J=7.0 Hz)

Example 9

Synthesis of 3-{3-[4-(2,6-diisobutyryloxyisonicotinoyloxy)-5-chloro-2-pyridyloxycarbonyl]benzoyl}-1-ethoxymethyl-5-fluorouracil (Compound I-8)

Compound I-2 (5.0 g) obtained in Example 2 was dissolved in 1,2-dimethoxyethane (75 mL). Isobutyryl chloride (3.07 mL) and pyridine (1.99 mL) were added thereto under ice cooling and reacted at the same temperature for 30 minutes. The solvents were evaporated from the resulting reaction product. Subsequently, water was added to the reaction product, and the mixture was separated by ethyl acetate. The organic layer was dried with sodium sulfate, and the solvent was then evaporated. The residue was purified by silica gel column chromatography (eluted with chloroform) to obtain Compound I-8 (5.37 g; yield: 87%).
$^1$H-NMR (CDCl$_3$, δPPM):
8.64 (1H, t, J=1.5 Hz), 8.56 (1H, s), 8.52 (1H, td, J=7.9 Hz, J=1.5 Hz), 8.29 (1H, td, J=8.0 Hz, J=1.5 Hz), 7.74 (2H, s), 7.73 (1H, t, J=7.7 Hz), 7.52 (1H, d, J=5.3 Hz), 7.34 (1H, s), 5.18 (2H, s), 3.64 (2H, q, J=7.1 Hz), 2.89 (2H, hept, J=6.9 Hz), 1.36 (12H, d, J=7.1 Hz), 1.21 (3H, t, J=6.3 Hz)

Example 10

Synthesis of 3-{3-[4-(2,6-dicyclopentanecarbonyloxyisonicotinoyloxy)-5-chloro-2-pyridyloxycarbonyl]benzoyl}-1-ethoxymethyl-5-fluorouracil (Compound I-9)

Compound I-9 was obtained by the same method as that used in Example 9, except that cyclopentanecarbonyl chloride was used instead of isobutyryl chloride.
$^1$H-NMR (CDCl$_3$, δPPM):
8.64 (1H, t, J=1.5 Hz), 8.55 (1H, s), 8.52 (1H, td, J=1.5 Hz, J=7.8 Hz), 8.29 (1H, td, J=1.6 Hz, J=8.4 Hz), 7.74 (2H, s), 7.73 (1H, t, J=7.8 Hz), 7.51 (1H, d, J=5.1 Hz), 7.33 (1H, s), 5.18 (2H, s), 3.65 (2H, q, J=7.1 Hz), 3.06 (2H, qu, J=8.1 Hz), 2.20-1.40 (16H, m), 1.24 (3H, t, J=7.1 Hz)

Example 11

Synthesis of 3-{3-[4-(2,6-diacetyloxyisonicotinoyloxy)-5-chloro-2-pyridyloxycarbonyl]benzoyl}-1-ethoxymethyl-5-fluorouracil (Compound I-10)

Compound I-10 was obtained by the same method as that used in Example 9, except that acetyl chloride was used instead of isobutyryl chloride.
$^1$H-NMR (CDCl$_3$, 522M):
8.64 (1H, t, J=1.5 Hz), 8.56 (1H, s), 8.52 (1H, td, J=8.0 Hz, J=1.4 Hz), 8.29 (1H, td, J=8.0 Hz, J=1.6 Hz), 7.78 (2H, s), 7.73 (1H, t, J=7.7 Hz), 7.51 (1H, d, J=5.3 Hz), 7.35 (1H, s), 5.18 (2H, s), 3.64 (2H, q, J=7.0 Hz), 2.38 (6H, s), 1.24 (3H, t, J=7.0 Hz)

Example 12

Synthesis of 3-{3-[4-(2,6-dipropionyloxyisonicotinoyloxy)-5-chloro-2-pyridyloxycarbonyl]benzoyl}-1-ethoxymethyl-5-fluorouracil (Compound I-11)

Compound I-11 was obtained by the same method as that used in Example 9, except that propionyl chloride was used instead of isobutyryl chloride.
$^1$H-NMR (CDCl$_3$, δPPM):
8.63 (1H, t, J=1.8 Hz), 8.55 (1H, s), 8.52 (1H, d, J=7.9 Hz), 8.29 (1H, d, J=7.9 Hz), 7.77 (2H, s), 7.73 (1H, t, J=7.8 Hz), 7.51 (1H, d, J=5.3 Hz), 7.35 (1H, s), 5.18 (2H, s), 3.64 (2H, q, J=7.0 Hz), 2.69 (4H, q, J=7.5 Hz), 1.32-1.21 (9H, m)

Example 13

Synthesis of 3-{3-[4-(2,6-dipivaloyloxyisonicotinoyloxy)-5-chloro-2-pyridyloxycarbonyl]benzoyl}-1-ethoxymethyl-5-fluorouracil (Compound I-12)

Compound I-12 was obtained by the same method as that used in Example 9, except that pivaloyl chloride was used instead of isobutyryl chloride.
$^1$H-NMR (CDCl$_3$, δPPM):
8.64 (1H, t, J=1.5 Hz), 8.56 (1H, s), 8.52 (1H, dt, J=1.5 Hz, 7.7 Hz), 8.29 (1H, dt, J=1.6 Hz, J=7.9 Hz), 7.73 (1H, t, J=7.9 Hz), 7.69 (2H, s), 7.51 (1H, d, J=5.3 Hz), 7.33 (1H, s), 5.19 (2H, s), 3.65 (2H, q, J=7.0 Hz), 1.41 (18H, s), 1.24 (3H, t, J=7.0 Hz)

Example 14

3-{3-[4-(2,6-dibenzoyloxynicotinoyloxy)-5-chloro-2-pyridyloxycarbonyl]benzoyl}-1-ethoxymethyl-5-fluorouracil (Compound I-13)

Compound I-13 was obtained by the same method as that used in Example 9, except that benzoyl chloride was used instead of isobutyryl chloride.
$^1$H-NMR (CDCl$_3$, δPPM):

8.64 (1H, s), 8.56 (1H, s), 8.53 (1H, d, J=7.9 Hz), 8.30 (1H, d, J=8.2 Hz), 8.24 (5H, d, J=6.6 Hz), 7.91 (2H, s), 7.77-7.65 (3H, m), 7.56-7.39 (6H, m), 5.18 (2H, s), 3.64 (2H, q, J=7.0 Hz), 1.24 (3H, t, J=7.0 Hz)

Example 15

Synthesis of 3-{3-[4-(2,6-di-p-chlorobenzoyloxy-isonicotinoyloxy)-5-chloro-2-pyridyloxycarbonyl]benzoyl}-1-ethoxymethyl-5-fluorouracil (Compound I-14)

Compound I-14 was obtained by the same method as that used in Example 9, except that p-chlorobenzoyl chloride was used instead of isobutyryl chloride.

$^1$H-NMR (CDCl$_3$, δPPM):
8.64 (1H, s), 8.57 (1H, s), 8.52 (1H, d, J=7.9 Hz), 8.29 (1H, d, J=7.9 Hz), 8.18 (4H, d, J=8.6 Hz), 8.03 (1H, d, J=8.4 Hz), 7.96 (2H, s), 7.74 (1H, t, J=7.8 Hz), 7.65-7.50 (4H, m), 7.38 (1H, s), 5.18 (2H, s), 3.64 (2H, q, J=7.0 Hz), 1.24 (3H, t, J=7.0 Hz)

Test Example 1

DPD Inhibitory Action and OPRT Inhibitory Action In Vitro (a) Test liquid preparation (1): Compound I-2 of the present invention was dissolved to a concentration of 10 mM in acetonitrile. The resulting product was diluted to concentrations of 1 mM, 100 µM, 10 µM, and 1 µM with a 10 mM potassium phosphate buffer solution (pH 6.0), thereby obtaining Test Liquids 1. The obtained Test Liquids 1 were separately added to the enzyme reaction solution described below to give final concentrations of 200 µM, 20 µM, 2 µM, and 0.2 µM.
(b) Test liquid preparation (2): As a DPD inhibitor, 5-chloro-2,4-dihydroxypyridine (CDHP; gimeracil) was dissolved to a concentration of 10 mM in a 10 mM potassium phosphate buffer solution (pH 6.0). The resulting product was diluted to concentrations of 1 mM, 100 µM, 10 µM, and 1 µM, thereby obtaining Test Liquids 2. The obtained Test Liquids 2 were separately added to the enzyme reaction solution to give final concentrations of 200 µM, 20 µM, 2 µM, and 0.2 µM.
(c) Test liquid preparation (3): As an OPRT inhibitor, citrazinic acid (Citra. A.) was dissolved to a concentration of 10 mM in 20 mM trishydroxyaminomethane-hydrochloric buffer solution (pH 8.0). Thereafter, the resulting product was diluted to concentrations of 1 mM, 100 µM, and 10 µM with a 10 mM potassium phosphate buffer solution, thereby obtaining Test Liquids (3). The obtained Test Liquids 3 were separately added to the enzyme reaction solution to give final concentrations of 200 µM, 20 µM, and 2 µM.
(d) Preparation of enzyme solution: The liver of an 8-week old SD rat was used as a DPD enzyme source, while human tumor cells that had been transplanted into a nude mouse and proliferated therein were used as an OPRT enzyme source. Specifically, immediately after a rat liver or successively-transplanted human tumor cells were extracted, a 50-mM tris-hydrochloric acid buffer solution (pH 8.0) containing 0.25 M saccharose, 5 mM magnesium chloride, and 1 mM dithreitol was added thereto to a concentration of 25% (w/v) and homogenized. Thereafter, ultracentrifugation was performed at 105,000 g for 60 minutes, and the obtained supernatant was used as a DPD enzyme solution or an OPRT enzyme solution.
(e) Enzyme reaction: A DPD enzyme reaction was carried out in accordance with the method of Tatsumi et al. (Gann, 78: 748-755 (1987)) using 5-FU labeled with tritium as a substrate. An OPRT enzyme reaction was carried out in accordance with the method of Shirasaka et al. (Cancer Res., 53: 4004-4009 (1993)) using 5-FU labeled with tritium as a substrate. Then, the activity of a control group (with no test compound) and test compound groups was measured. The percent inhibition of the test compound relative to DPD or OPRT was calculated using the following formula: [1-(the enzyme activity with the test compound/the enzyme activity of the control group)]×100(%). Tables 1 and 2 show the results.

TABLE 1

| | DPD Inhibitory Activity | | | | OPRT Inhibitory Activity | | |
|---|---|---|---|---|---|---|---|
| Drug | Conc. (µM) | Activity (nmol/ml/min) | Inhibition (%) | Drug | Conc. (µM) | Activity (nmol/ml/min) | Inhibition (%) |
| Control | — | 1.009 | — | Control | — | 0.376 | — |
| CDHP | 200 | 0.106 | 89.5 | Citra. A. | 200 | 0.075 | 80.0 |
| | 20 | 0.074 | 92.7 | | 20 | 0.173 | 54.0 |
| | 2 | 0.195 | 80.7 | | 2 | 0.301 | 20.0 |
| | 0.2 | 0.597 | 40.8 | | 0.2 | 0.379 | 0.0 |
| Compound I-2 | 200 | 0.100 | 90.0 | Compound I-2 | 200 | 0.069 | 81.6 |
| | 20 | 0.075 | 92.6 | | 20 | 0.168 | 55.3 |
| | 2 | 0.157 | 84.4 | | 2 | 0.280 | 25.5 |
| | 0.2 | 0.613 | 39.2 | | 0.2 | 0.375 | 0.0 |

TABLE 2

| | DPD Inhibition (%) | | | OPRT Inhibition (%) | |
|---|---|---|---|---|---|
| Drug | 0.2 µM | 2 µM | Drug | 0.2 µM | 2 µM |
| CDHP | 44.8 | 85.1 | Citra. A. | 31.9 | 75.1 |
| Compound I-10 | 43.9 | 77.2 | Compound I-10 | 27.8 | 76.4 |
| Compound I-9 | 45.7 | 74.6 | Compound I-9 | 41.2 | 75.9 |

(f) Test results: Compounds I-2, I-9, and I-10 of the present invention inhibited DPD activity and OPRT activity induced on 5-FU as a substrate in the enzyme reaction system in vitro. The inhibitory activity of the compounds of the present invention was almost equal to that of gimeracil or citrazinic acid, which served as the control. Although gimeracil and citrazinic acid have no antitumor activity, they do have DPD inhibitory activity or OPRT inhibitory activity. This confirmed that the antitumor agents of the present invention have high DPD inhibitory activity and high OPRT inhibitory activity.

Test Example 2

Inhibitory Effect of Compound I-2 on 5-FU Activation (Phosphorylation) in Cancer Cells (a) Test liquid preparation 1: Compound I-2 or I-10 of the present invention was dissolved to a concentration of 1 mM in cold physiological saline. The resulting product was further diluted 10-fold with physiological saline, yielding a 100-µM solution.
(b) Test liquid preparation 2: As an OPRT inhibitor, which inhibits the phosphorylation of 5-FU, citrazinic acid (Citra.A.) was dissolved to a concentration of 1 mM in cold physiological saline, and further diluted 10-fold with physiological saline, yielding a 100-μM solution.

(c) Preparation of cancer cell suspension: Ascites-type sarcoma 180 cells were preliminarily transplanted intraperitoneally into an ICR mouse and proliferated therein for use in the test as raw (intact) cells. The proliferated cells were isolated and then washed with physiological saline. Cell pellets were collected, suspended at $1.25 \times 10^7$ cells/mL in Hanks medium, and immediately used in the test.

(d) Experiment on inhibition of intracellular phosphorylation of 5-FU: 0.1 mL of each test liquid and 0.1 mL of a 10-μM 5-FU solution were added to 0.8 mL of sarcoma 180 cells in ice and incubated at 37° C. for 30 minutes. Immediately after the completion of the reaction, 4 mL of a cold Hanks solution was added to the reaction solution, and the cells were washed and separated by centrifugation. After this procedure was repeated twice, 2 mL of a cold 5% trichloroacetic acid (TCA) solution was added to the cell pellet to disrupt the cells, and 5-FU and its nucleotide metabolites were extracted. Subsequently, a portion of the nucleic acid extract was applied to a silica gel $60F_{254}$ plate and developed with a mixed liquid comprising chloroform-methanol-acetic acid (17:3:1) to isolate the nucleotide moiety. The radioactivity thereof was measured and the concentration of 5-FU phosphorylation was measured. Under the above-described conditions, the percent inhibition of Test Liquids 1 and 2 on 5-FU phosphorylation relative to a control group (with no test liquid) was calculated. Table 3 shows the results.

TABLE 3

| Drug | Conc. (μm) | F-nucleotides (pmol/1 × $10^7$ cells) | % Inhibition |
| --- | --- | --- | --- |
| Control | 0 | 60.93 | — |
| Compound I-2 | 10 | 47.26 | 22.4 |
|  | 100 | 28.88 | 52.6 |
| CTA | 10 | 55.78 | 8.5 |
|  | 100 | 51.72 | 15.1 |
| Control | 0 | 63.32 | — |
| Compound I-10 | 10 | 40.71 | 35.7 |
|  | 100 | 27.62 | 56.4 |
| CTA | 10 | 62.19 | 1.8 |
|  | 100 | 60.13 | 5.1 |

CTA: Citrazinic acid (e) Test results: Compounds I-2 and I-10 of the present invention inhibited, in a concentration dependent manner, the intracellular phosphorylation of 3-FU during the reaction for 30 minutes; at a concentration of 10 μM, the percent inhibition was about 20 to 30%, and at a concentration of 100 μM, the percent inhibition was 50 to 60%. In contrast, citrazinic acid, which served as the control, exhibited almost no inhibition on the 5-FU intracellular phosphorylation through the reaction for 30 minutes; even at a concentration of 100 μM, the percent inhibition was only 5 to 15%. The above results confirm that the compounds of the present invention after being taken up by the cells inhibit the 5-FU phosphorylation induced by OPRT, in a dose-dependent manner.

Test Example 3

Antitumor Effects and Side Effects in Human-Tumor Cell Transplanted Mouse (a) Test liquid preparation 1: Compound I-2 of the present invention was suspended at a concentration of 1.5, 2.25, or 3.0 mg/mL in a 0.5% (w/v) hydroxypropylmethylcellulose (hereinafter simply referred to as "HPMC") solution, and stirred with a stirrer at room temperature for about 10 minutes. Thereafter, ultrasonic treatment was performed under ice cooling for about 5 minutes, thereby obtaining a Compound I-2 drug liquid to be used at a dose of 15 mg/kg/day, 22.5 mg/kg/day, or 30 mg/kg/day.

(b) Test liquid preparation 2: Compound I-10 of the present invention was suspended at a concentration of 2.57, 3.42, or 42.8 mg/mL in a 0.5% (w/v) HPMC solution, and stirred with a stirrer at room temperature for about 10 minutes. Thereafter, ultrasonic treatment was performed under ice cooling for about 5 minutes, thereby obtaining a Compound I-10 drug liquid to be used at a dose of 25.7 mg/kg/day, 34.2 mg/kg/day, or 42.8 mg/kg/day.

(c) Test liquid preparation 3: Among the compounds of the present invention, a test substance (Compound 8a) that does not contain a citrazinic acid moiety was suspended at a concentration of 1.15, 1.73, or 2.3 mg/mL in a 0.5% (w/v) HPMC solution and stirred with a stirrer at room temperature for about 10 minutes. Thereafter, ultrasonic treatment was performed under ice cooling for about 5 minutes, thereby obtaining a Compound 8a drug liquid to be used at a dose of 11.5 mg/kg/day, 17.3 mg/kg/day, or 23 mg/kg/day.

(d) Test liquid preparation 4: S-1 (U.S. Pat. No. 2,614,164), which is a combination agent comprising tegafur-gimeracil-oteracil potassium at a molar ratio of 1:0.4:1, was suspended in a 0.5% (w/v) HPMC solution so that the amount of tegafur was 0.5, 0.75, or 1.0 mg/mL. The resulting product was stirred with a stirrer at room temperature for about 10 minutes. Thereafter, ultrasonic treatment was performed under ice cooling for about 5 minutes, thereby obtaining an S-1 drug liquid to be used at a dose of 5.0 mg/kg/day, 7.5 mg/kg/day, or 10 mg/kg/day.

(e) Test liquid preparation 5: Test substance BOF-A2 was suspended at a concentration of 1.4, 2.1, or 2.8 mg/mL in a 0.5% (w/v) HPMC solution and stirred with a stirrer at room temperature for about 10 minutes. Thereafter, ultrasonic treatment was performed under ice cooling for about 5 minutes, thereby obtaining a BOF-A2 drug liquid to be used at a dose of 14 mg/kg/day, 21 mg/kg/day, or 28 mg/kg/day.

(f) Experiment: The human gastric cancer strain (SC-2) was subcutaneously transplanted into the back of a BALB/cA-nu mouse and preliminarily proliferated therein. The proliferated strain was extracted, cut into about 2 mm square pieces with scissors in physiological saline, and subcutaneously inoculated to the right axillary region of mice of the same strain, 5 to 6 weeks of age, using a transplantation needle. The resulting mice were bred for adaptation at least for 1 to 2 weeks, and divided into a control group and test drug groups at three different doses (3 groups for Compound I-2; 3 groups for Compound I-10; 3 groups for Compound 8a; 3 groups for S-1; and 3 groups for BOF-A3), such that the average tumor volume and the average standard deviation (S. D.) were as equal as possible between the groups (5 to 6 mice per group) (day 0). Then, drug administration was initiated from the next day. Each of the test liquids shown in (a) to (e) above was administered orally to the mice in each of the test drug groups using a sonde for oral administration at a dose of 0.1 ml per 10 g body weight once a day for 14 continuous days. In the same manner as the above, the cancer-bearing mice in the control group were subjected to oral administration of only 0.5% HPMC liquid for 14 continuous days.

The tumor volume of each mouse in each group before the initiation of the treatment, on day 3, day 5, day 8 (1 week after), day 11, and day 15 (2 weeks after), i.e., after termination of the administration, was calculated using Equation 1 below, and respective relative tumor volume (RTV) relative to the tumor volume at the time of initiation of the treatment was calculated. In relation to the antitumor effect, the average value of the tumor proliferation inhibition ratio (IR; %) was calculated from the average tumor volume of each treatment group on day 15 (after termination of the treatment) relative to that of the control group on day 15, using Equation 2. In addition, the occurrence of diarrhea and death were observed through the treatment period of 15 days. The number of occurrences is shown in the tables. Along therewith, a weight change ratio was calculated from the body weight of the mice at the time of the termination of the drug administration relative to the body weight of the mice at the time of the initiation of the administration, using Equation 3. Table 4 shows the results.

$$\text{Tumor volume(mm}^3\text{)} = (\text{major axis}) \times (\text{minor axis})^2 \times \tfrac{1}{2} \qquad \text{Equation 1:}$$

$$\text{Tumor proliferation inhibition ratio(IR, \%)} = [1 - (\text{average tumor volume of treatment group})/(\text{average tumor volume of control group})] \times 100 \qquad \text{Equation 2:}$$

$$\text{Average weight change ratio(\%)} = [(\text{average weight on Day 15}) - (\text{average weight on Day 1})]/(\text{average weight on Day 1}) \times 100 \qquad \text{Equation 3:}$$

TABLE 4

| Test Drug | Dosage (mg/kg/day) | Number (N) | Tumor proliferation inhibition ratio (%) | Average weight change (%) | Diarrhea (N) | Death (N) |
|---|---|---|---|---|---|---|
| Compound I-2 | 15.0 | 5 | 41.1 | −1.13 | 0 | 0 |
|  | 22.5 | 5 | 56.0 | −4.18 | 0 | 0 |
|  | 30.0 | 5 | 67.9 | 1.76 | 0 | 0 |
| Compound I-10 | 25.7 | 6 | 31.9 | 1.97 | 0 | 0 |
|  | 34.2 | 6 | 51.0 | −0.05 | 0 | 0 |
|  | 42.8 | 6 | 57.7 | −4.31 | 0 | 0 |
| Compound 8a | 11.5 | 5 | 52.8 | 0.34 | 0 | 0 |
|  | 17.3 | 5 | 58.1 | 2.32 | 0 | 0 |
|  | 23.0 | 5 | 77.7 | −18.11 | 4 | 1 |
| BOF-A2 | 14 | 6 | 51.0 | 3.16 | 0 | 0 |
|  | 21 | 6 | 70.9 | −7.48 | 0 | 0 |
|  | 28 | 6 | 72.4 | −20.58 | 3 | 1 |
| S-1 | 5 | 6 | 54.0 | −0.09 | 0 | 0 |
|  | 7.5 | 6 | 60.0 | −4.08 | 0 | 0 |
|  | 10 | 6 | 79.4 | −1.84 | 0 | 0 |

Test results: Compounds I-2 and I-10 of the present invention showed high antitumor effects in a dose-dependent manner. In addition, significant weight loss in mice was not observed, and diarrhea or toxic death in mice was also not observed. This confirms that Compounds I-2 and I-10 of the present invention exhibit a high antitumor effect with reduced toxicity. In contrast, regarding Compound 8a, which is equal to the compounds of the present invention but does not contain citrazinic acid, the antitumor effect increased in a dose-dependent manner in the dosage range employed in this test, but a significant weight loss, diarrhea, and death in mice were observed. BOF-A2 exhibited an antitumor effect and toxicity similar to those of Compound 8a, which is equal to the compounds of the present invention but does not contain citrazinic acid. Specifically, BOF-A2 at a dose that exhibits a high antitumor effect caused significant weight loss, diarrhea, and toxic death in mice. Similar to compounds of the present invention, S-1, in which gimeracil (a DPD inhibitor) and oteracil potassium (an agent that reduces gastrointestinal toxicity) are added to tegafur (a 5-FU derivative), exhibited an antitumor effect in a dose-dependent manner and did not cause a significant weight loss or diarrhea in mice, when administered at doses less than 12.5 mg/kg/day, which is considered an overdose.

As is clear from the above, the compounds of the present invention have an excellent antitumor effect and an effect of reducing side effects. Such effects are almost equal to those of S-1, whose usefulness is widely recognized in the field of antitumor agents.

Contrary to S-1, which is a combination drug comprising three agents, the compound of the present invention is in the form of a single compound. Therefore, variations in pharmacokinetics of the metabolite are expected to be small among patients. Specifically, in the case where a combination of three agents, which aims to increase the antitumor effect of 5-FU while alleviating side effects, in particular, gastrointestinal toxicity, is used, each component is generally independently absorbed and distributed, causing variations in pharmacokinetics among patients. These variations cause variations in 5-FU concentration, possibly resulting in a case where a favorable balance between the antitumor effects and toxicity cannot be established. In contrast, a drug in the form of a single compound, which is designed to achieve the above-mentioned objects, will be absorbed through gastrointestinal tissue, after which it will be promptly activated in the body, and will exert its functions (5-FU release from a masked form, DPD inhibition, suppression of gastrointestinal disorders). Therefore, the difference in variation in metabolism pharmacokinetics of the active metabolites in vivo among patients is assumed to be smaller than that of a combination drug.

Test Example 4

DPD Inhibitory Action and OPRT Inhibitory Action of Compound I-11 in vitro (a) Test liquid preparation (1): Compound I-11 of the present invention was dissolved to a concentration of 10 mM in acetonitrile. The resulting product was diluted to concentrations of 1 mM, 100 μM, 10 μM, and 1 μM with a 10 mM potassium phosphate buffer solution (pH 6.0), thereby obtaining Test Liquids 1. The obtained Test Liquids 1 were separately added to the enzyme reaction solution described below to give final concentrations of 200 μM, 20 μM, 2 μM, and 0.2 μM.

(b) Preparation of enzyme solution: The liver of an 8-week old SD rat was used as a DPD enzyme source, while human tumor cells that had been transplanted into a nude mouse and proliferated therein were used as an OPRT enzyme source. Specifically, immediately after a rat liver or successively-transplanted human tumor cells were extracted, a 50-mM tris-hydrochloric acid buffer solution (pH 8.0) containing 0.25 M saccharose, 5 mM magnesium chloride, and 1 mM dithreitol was added thereto to a concentration of 25% (w/v) and homogenized. Thereafter, ultracentrifugation was performed at 105,000 g for 60 minutes, and the obtained supernatant was used as a DPD enzyme solution or an OPRT enzyme solution.

(c) Enzyme reaction: A DPD enzyme reaction was carried out in accordance with the method of Tatsumi et al. (Gann, 78: 748-755 (1987)) using 5-FU labeled with tritium as a substrate. An OPRT enzyme reaction was carried out in accordance with the method of Shirasaka et al. (Cancer Res., 53: 4004-4009 (1993)) using 5-FU labeled with tritium as a substrate. Then, the activity of a control group (with no test compound) and test compound groups was measured. The percent inhibition of the test compound relative to DPD or OPRT was calculated using the following formula: [1-(the enzyme activity with the test compound/the enzyme activity of the control group)]×100(%). Table 5 shows the results.

TABLE 5

| | DPD Inhibitory Activity | | | | OPRT Inhibitory Activity | | |
|---|---|---|---|---|---|---|---|
| Drug | Conc. (μM) | Activity (nmol/ml/min) | Inhibition (%) | Drug | Conc. (μM) | Activity (nmol/ml/min) | Inhibition (%) |
| Control | — | 0.659 | — | Control | — | 0.369 | — |
| Compound I-11 | 20 | 0.081 | 87.7 | Compound I-11 | 20 | 0.046 | 87.5 |
| | 2 | 0.216 | 67.2 | | 2 | 0.098 | 73.4 |
| | 0.2 | 0.285 | 56.8 | | 0.2 | 0.101 | 42.6 |
| | 0.02 | 0.705 | 0.0 | | | | |

(d) Test results: Compound I-11 of the present invention inhibited DPD activity and OPRT activity induced on 5-FU as a substrate in the enzyme reaction system in vitro. The $IC_{50}$ values thereof were about 0.5 μM and 15 μM, respectively. The inhibitory activity of the compound of the present invention was almost equal to that of gimeracil or citrazinic acid, which served as the control. Although gimeracil and citrazinic acid have no antitumor activity, they have DPD inhibitory activity or OPRT inhibitory activity. Based on this, the antitumor agents of the present invention are confirmed to have high DPD inhibitory activity and high OPRT inhibitory activity.

Test Example 5

Inhibitory Effect of Compounds I-9, I-11, I-12, and I-13 on 5-FU Activation (Phosphorylation) in Cancer Cells (a) Test liquid preparation 1: Compounds I-9, I-11, I-12, and I-13 of the present invention were separately dissolved to a concentration of 1 mM in cold physiological saline. Each of the resulting products was further diluted 10-fold with physiological saline, yielding a 100-μM solution.

(b) Test liquid preparation 2: As an OPRT inhibitor, which inhibits the phosphorylation of 5-FU, citrazinic acid was dissolved to a concentration of 1 mM in cold physiological saline, and further diluted 10-fold with physiological saline, yielding a 100-μM solution.

(c) Preparation of cancer cell suspension: Ascites-type sarcoma 180 cells were preliminarily transplanted intraperitoneally into an ICR mouse and proliferated therein for use in the test as raw (intact) cells. The proliferated cells were isolated and then washed with physiological saline. Cell pellets were collected, suspended at $1.25 \times 10^7$ cells/mL in Hanks medium, and immediately used in the test.

(d) Experiment on inhibition of intracellular phosphorylation of 5-FU: 0.1 mL of each test liquid and 0.1 mL of a 10-μM 5-FU solution were added to 0.8 mL of sarcoma 180 cells in ice and incubated at 37° C. for 15 or 30 minutes. Immediately after the completion of the reaction, 4 mL of a cold Hanks solution was added to the reaction solution, and the cells were washed and separated by centrifugation. After this procedure was repeated twice, 2 mL of a cold 5% trichloroacetic acid (TCA) solution was added to the cell pellet to disrupt the cells, and 5-FU and its nucleotide metabolites were extracted. Subsequently, a portion of the nucleic acid extract was applied to a silica gel $60F_{254}$ plate and developed with a mixed liquid comprising chloroform-methanol-acetic acid (17:3:1) to isolate the nucleotide moiety. The radioactivity thereof was measured and the concentration of 5-FU phosphorylation was measured. Under the above-described conditions, the percent inhibition of Test Liquids 1 and 2 on 5-FU phosphorylation relative to a control group (with no test liquid) was calculated. Table 6 shows the results.

TABLE 6

Inhibitory Effect of the Compounds of the Present Invention on Phosphorylation of 5-FU in Cancer Cells

| Drug | Conc. (μm) | RNA Fraction (pmol/1 × 10⁷ cells) (30 min. Incubation) | Inhibition (%) |
|---|---|---|---|
| Control | — | 63.32[#] | — |
| I-9 | 10 | 27.42 | 56.7 |
| | 100 | 23.61 | 62.7 |
| I-12 | 10 | 28.15 | 55.5 |
| | 100 | 25.48 | 59.8 |
| I-13 | 10 | 26.63 | 58.1 |
| | 100 | 25.68 | 59.4 |
| I-11 | 10 | 40.71 | 35.7 |
| | 100 | 27.62 | 56.4 |
| CTA | 10 | 62.19 | 1.8 |
| | 100 | 60.13 | 5.0 |

5-FU concentration: 2 μM (containing 2 μCi of ³H-FU) in assay mixture
[#]Mean value of duplicate tests (e) Test results: The compounds of the present invention (I-9, I-11, I-12, and I-13) inhibited the intracellular phosphorylation of 5-FU in a concentration-dependent manner when the reaction was carried out for 30 minutes; at a concentration of 10 μM, the percent inhibition was about 35 to 57%, and at a concentration of 100 μM, the percent inhibition was 56 to 63%. In contrast, citrazinic acid, which served as the control, exhibited almost no inhibition on the 5-FU intracellular phosphorylation through the reaction for 30 minutes; even at a concentration of 100 μM, the percent inhibition was only 5%. The above results confirm that the compounds of the present invention after being taken up by the cells inhibit the 5-FU phosphorylation induced by OPRT, in a dose-dependent manner.

Test Example 6

Antitumor Effects and Side Effects in Human-Tumor Cell Transplanted Mouse (a) Test liquid preparation 1: Compound I-11 of the present invention was suspended at a concentration of 2.67, 3.56, or 4.45 mg/mL in a 0.5% (w/v) HPMC solution, and stirred with a stirrer at room temperature for about 10 minutes. Thereafter, ultrasonic treatment was performed under ice cooling for about 5 minutes, thereby obtaining a Compound I-11 drug liquid to be used at a dose of 26.7 mg/kg/day, 35.6 mg/kg/day, or 44.5 mg/kg/day.

(b) Test liquid preparation 2: Compound I-9 of the present invention was suspended at a concentration of 4.95 mg/mL in a 0.5% (w/v) HPMC solution, and stirred with a stirrer at room temperature for about 10 minutes. Thereafter, ultrasonic treatment was performed under ice cooling for about 5 minutes, thereby obtaining a Compound I-9 drug liquid to be used at a dose of 49.5 mg/kg/day.

(c) Test liquid preparation 3: S-1 was suspended in a 0.5% (w/v) HPMC solution so that the amount of tegafur was 0.5, 0.75, or 1.0 mg/mL. The resulting product was stirred with a stirrer at room temperature for about 10 minutes. Thereafter, ultrasonic treatment was performed under ice cooling for about 5 minutes, thereby obtaining an S-1 drug liquid to be used at a dose of 5.0 mg/kg/day, 7.5 mg/kg/day, or 10 mg/kg/day.

(d) Experiment: The human gastric cancer strain (SC-2) was subcutaneously transplanted into the back of a BALB/cA-nu mouse and preliminarily proliferated therein. The proliferated strain was extracted, cut into about 2 mm square pieces with scissors in physiological saline, and subcutaneously inoculated to the right axillary region of mice of the same strain, 5 to 6 weeks of age, using a transplantation needle. The resulting mice were bred for adaptation at least for 1 to 2 weeks, and divided into a control group and test drug groups at three different doses (3 groups for I-9; 3 groups for Compound I-11; and 3 groups for S-1), such that the average tumor volume and the average standard deviation (S. D.) were as equal as possible between the groups (6 mice per group) (day 0). Then, drug administration was initiated from the next day. Each of the test liquids shown in (a) to (c) above was administered orally to the mice in each of the test drug groups using a sonde for oral administration at a dose of 0.1 ml per 10 g body weight once a day for 14 continuous days. In the same manner as the above, the cancer-bearing mice in the control group were subjected to oral administration of only 0.5% HPMC liquid for 14 continuous days.

The tumor volume of each mouse in each group before the initiation of the treatment, on day 3, day 5, day 8 (1 week after), day 11, and day 15 (2 weeks after), i.e., after termination of the administration, was calculated using Equation 1 below, and respective relative tumor volume (RTV) relative to the tumor volume at the time of initiation of the treatment was calculated. In relation to the antitumor effect, the average value of the tumor proliferation inhibition ratio (IR; %) was calculated from the average tumor volume of each treatment group on day 15 (after termination of the treatment) relative to that of the control group on day 15, using Equation 2. Table 1 shows the results. In addition, the occurrence of diarrhea and death were observed through the treatment period of 15 days. The number of occurrences is shown. Along therewith, a weight change ratio was calculated from the body weight of the mice at the time of the termination of the drug administration relative to the body weight of the mice at the time of the initiation of the administration, using Equation 3.

Tumor volume(mm³)=(major axis)×(minor axis)²×½    Equation 1:

Tumor proliferation inhibition ratio(IR, %)=[1−(average tumor volume of treatment group)/(average tumor volume of control group)]×100    Equation 2:

Average weight change ratio(%)=[(average weight on Day 15)−(average weight on Day 1)]/(average weight on Day 1)×100    Equation 3:

TABLE 7

Antitumor Effects and Side Effects of the compounds of the present invention and S-1 in SC-2 Transplanted Mouse (Body Weight Change, Diarrhea, and Death)

| Drug | Dosage (mg/kg) | N | IR (%) | BWC (% initial) | Diarrhea (N) | Death (N) |
|---|---|---|---|---|---|---|
| Control | — | 6 | — | +2.93 | 0 | 0 |
| I-11 | 26.7* | 6 | 17.0 | +1.68 | 0 | 0 |
|  | 35.6** | 6 | 32.0 | +1.82 | 0 | 0 |
|  | 44.5*** | 6 | 47.3 | −3.94 | 0 | 0 |

TABLE 7-continued

Antitumor Effects and Side Effects of the compounds of the present invention and S-1 in SC-2 Transplanted Mouse (Body Weight Change, Diarrhea, and Death)

| Drug | Dosage (mg/kg) | N | IR (%) | BWC (% initial) | Diarrhea (N) | Death (N) |
|---|---|---|---|---|---|---|
| I-9 | 49.5*** | 6 | 29.5 | +4.67 | 0 | 0 |
| S-1 | 7.5 | 6 | 76.7 | −1.89 | 0 | 0 |
|  | 10.0 | 6 | 83.1 | −8.82 | 2 | 0 |
|  | 12.5 | 6 | 88.0 | −28.28 | 3 | 2 |

Regarding the dosages of Compounds I-9 and I-11,
*is equivalent to 7.5 mg/kg of S-1,
**is equivalent to 10 mg/kg of S-1, and
***is equivalent to 12.5 mg/kg of S-1.

Test results: Compound I-11 of the present invention showed high antitumor effects in a dose-dependent manner over the dosage range of 26.7 to 44.5 mg/kg/day. In addition, a significant weight loss in mice was not observed, and diarrhea or toxic death in mice was also not observed. This confirms that Compound I-11 of the present invention exhibits a high antitumor effect with reduced toxicity. Compound I-9 of the present invention also showed an antitumor effect at a dose of 49.5 mg/kg/day; further, weight loss, diarrhea, and toxic death were not observed at the same dose. Similar to Compound I-11 of the present invention, S-1, in which gimeracil (a DPD inhibitor) and oteracil potassium (an agent that reduces gastrointestinal toxicity) are added to tegafur (a 5-FU derivative), showed an antitumor effect in a dose-dependent manner; however, significant weight loss, diarrhea, and toxic death were observed in a dose-dependent manner.

Test Example 7

Antitumor Effects and Side Effects in Human-Tumor Cell Transplanted Rat (1)

(a) Test liquid preparation 1: Compound I-11 of the present invention was suspended at a concentration of 7.12, or 8.01 mg/mL in a 0.5% (w/v) HPMC solution, and stirred with a stirrer at room temperature for about 10 minutes. Thereafter, ultrasonic treatment was performed under ice cooling for about 5 minutes, thereby obtaining a Compound I-11 drug liquid to be used at a dose of 71.2 mg/kg/day or 80.1 mg/kg/day.

(b) Test liquid preparation 2: S-1, which is a combination agent comprising tegafur-gimeracil-oteracil potassium at a molar ratio of 1:0.4:1, was suspended in a 0.5% (w/v) HPMC solution so that the amount of tegafur was 2.0 or 2.25 mg/mL. The resulting product was stirred with a stirrer at room temperature for about 10 minutes. Thereafter, ultrasonic treatment was performed under ice cooling for about 5 minutes, thereby obtaining an S-1 drug liquid to be used at a dose of 20.0 mg/kg/day or 22.5 mg/kg/day.

(c) Experiment: The human gastric cancer strain (SC-2) was subcutaneously transplanted into the back of a nude rat and preliminarily proliferated therein. The proliferated strain was extracted, cut into about 2 to 3 mm square pieces with scissors in physiological saline, and subcutaneously inoculated to the right axillary region of rats of the same strain, 5 to 6 weeks of age, using a transplantation needle. The resulting rats were bred for adaptation at least for 1 to 2 weeks, and divided into a control group and test drug groups at two different doses (2 groups for Compound I-11; and 2 groups for S-1), such that the average tumor volume and the average standard deviation (S. D.) were as equal as possible between the groups (5 to 6 rats per group) (day 0). Then, drug administration was initiated from the next day. Each of the test liquids shown in (a) to (b) above was administered orally to the rats in each of the test drug groups using a sonde for oral administration at a dose of 0.1 ml per 10 g body weight once a day for 14 continuous days. In the same manner as the above, the cancer-bearing rats in the control group were subjected to oral administration of only 0.5% HPMC liquid for 14 continuous days.

The tumor volume of each rat in each group before the initiation of the treatment, on day 3, day 5, day 8 (1 week after), day 11, and day 15 (2 weeks after), i.e., after termination of the administration, was calculated using Equation 1 below, and respective relative tumor volume (RTV) relative to the tumor volume at the time of initiation of the treatment was calculated. In relation to the antitumor effect, the average value of the tumor proliferation inhibition ratio (IR; %) was calculated from the average tumor volume of each treatment group on day 15 (after termination of the treatment) relative to that of the control group on day 15, using Equation 2. Table 1 shows the results. In addition, the occurrence of diarrhea and death were observed through the treatment period of 15 days. The number of occurrences is shown. Along therewith, a weight change ratio was calculated from the body weight of the rats at the time of the termination of the drug administration relative to the body weight of the rats at the time of the initiation of the administration, using Equation 3.

$$\text{Tumor volume(mm}^3\text{)}=(\text{major axis})\times(\text{minor axis})^2\times\tfrac{1}{2} \quad \text{Equation 1:}$$

$$\text{Tumor proliferation inhibition ratio(IR, \%)}=[1-(\text{average tumor volume of treatment group})/(\text{average tumor volume of control group})]\times 100 \quad \text{Equation 2:}$$

$$\text{Average weight change ratio(\%)}=[(\text{average weight on Day 15})-(\text{average weight on Day 1})]/(\text{average weight on Day 1})\times 100 \quad \text{Equation 3:}$$

(d) Hematological toxicity: All of the rats in relation to which antitumor effects, body weight changes, and macroscopic side effects were observed in Experiment (c) above were anesthetized with ether. Then, an incision was made in the abdomen, and a blood sample was collected from each rat via inferior vena cava with a 5 ml syringe. A coagulation inhibitor was added to each of the collected blood samples, and the white blood cell count, red blood cell count, and platelet count were measured using a hemocytometer. The average value of the six rats each of the control group, the Compound I-11 groups, and the S-1 groups were calculated, and these average values were compared with each other.

(e) Test results 1: FIG. 1-1 shows the results of the antitumor effects of S-1 and Compound I-11 and changes in the body weight. Compound I-11 of the present invention showed high antitumor effects in a dose-dependent manner over the dosage range of 71 to 88 mg/kg/day. In addition, significant weight loss in mice was not observed, and diarrhea or toxic death in rats was also not observed. This confirms that Compound I-11 of the present invention exhibits a high antitumor effect with reduced toxicity. Similar to the compound of the present invention, S-1, in which gimeracil (a DPD inhibitor) and oteracil potassium (an agent that reduces gastrointestinal toxicity) are added to tegafur (a 5-FU derivative), exhibited an antitumor effect in a dose-dependent manner, and did not cause weight loss or diarrhea, which were used as an index of side effects.

Figures 1, 2:
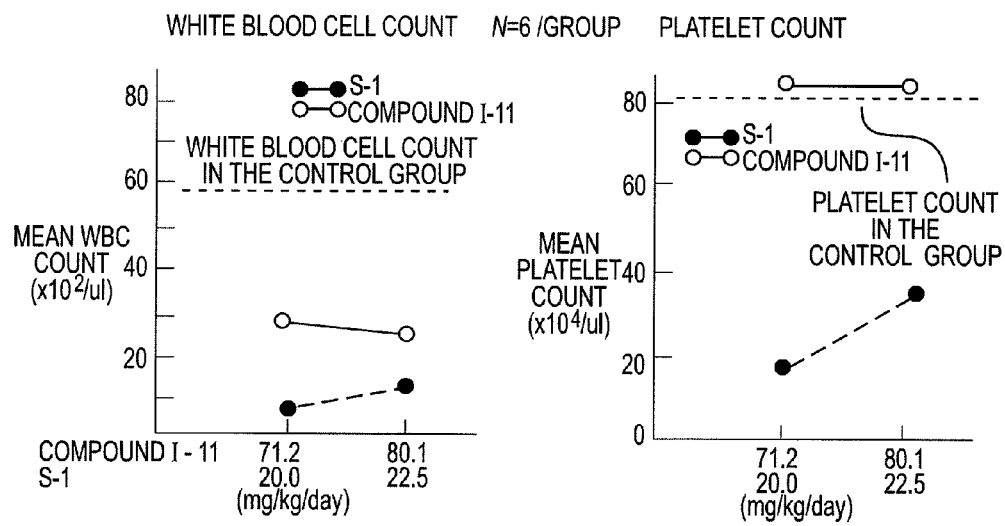
Figures 1, 2:
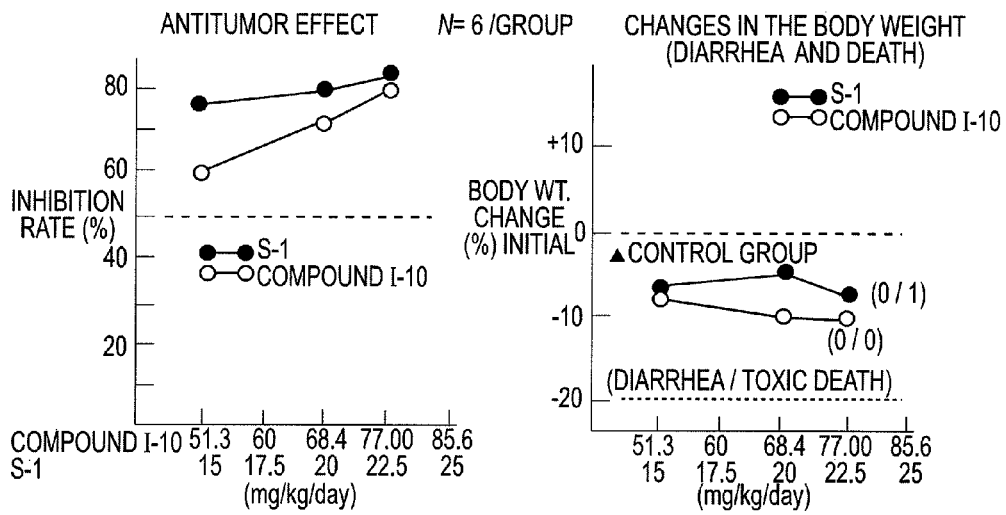
Figure 2:
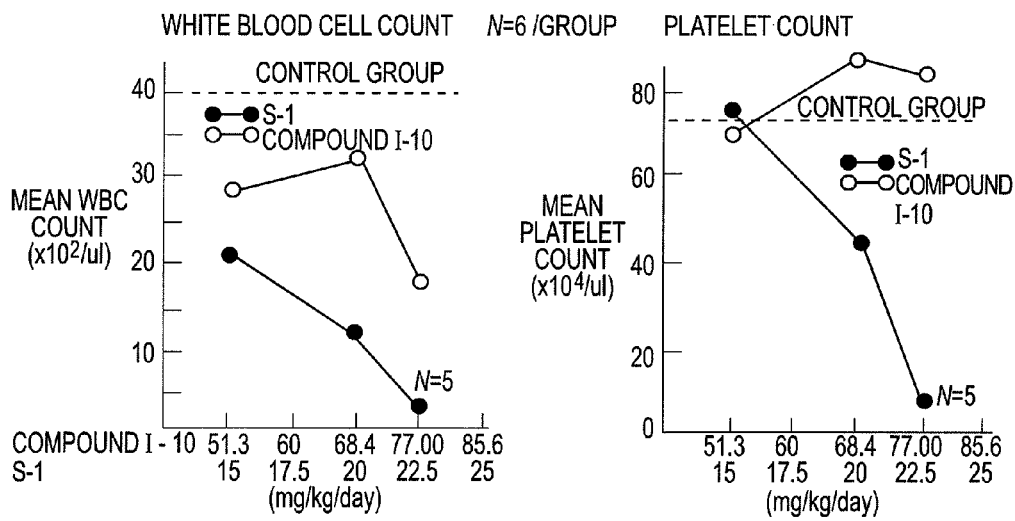

(f) Test results 2: FIG. 1-2 shows the results of the white blood cell count and the platelet count after administration of S-1 and Compound I-11. The white blood cell count of cancer-bearing rats, to which Compound I-11 at a dose of 71 to 88 mg/kg/day was orally administered for 2 weeks, was reduced to about 50% of that of the control group. In contrast, the white blood cell count of rats to which S-1 at a dose of 20 to 22.5 mg/kg/day was administered for 2 weeks, similar to the above, was reduced to ⅙ of that of the control group. Accordingly, it is clear that Compound I-11 of the present invention reduced the white blood cell count less. Further, the platelet count of rats to which S-1 was administered was reduced from ¼ to ⅓ of that of the control group; whereas the platelet count of rats to which Compound I-11 was administered was almost the same as that of the control group. These results reveal that although Compound I-11 of the present invention and S-1 exhibit similar antitumor effects and showed similar results in side effects such as diarrhea and weight loss, Compound I-11 has a considerably lower hematological toxicity.

Test Example 8

Antitumor Effects and Side Effects in Human-Tumor Cell Transplanted Rat (2)

(a) Test liquid preparation 1: Compound I-10 of the present invention was suspended at a concentration of 5.13, 6.84, or 7.70 mg/mL in a 0.5% (w/v) HPMC solution, and stirred with a stirrer at room temperature for about 10 minutes. Thereafter, ultrasonic treatment was performed under ice cooling for about 5 minutes, thereby obtaining a Compound I-10 drug liquid to be used at a dose of 51.3 mg/kg/day, 68.4 mg/kg/day, or 77.0 mg/kg/day.

(b) Test liquid preparation 2: S-1, which is a combination agent comprising tegafur-gimeracil-oteracil potassium at a molar ratio of 1:0.4:1, was suspended in a 0.5% (w/v) HPMC solution so that the amount of tegafur was 1.5, 2.0, or 2.25 mg/mL. The resulting product was stirred with a stirrer at room temperature for about 10 minutes. Thereafter, ultrasonic treatment was performed under ice cooling for about 5 minutes, thereby obtaining an S-1 drug liquid to be used at a dose of 15.0 mg/kg/day, 20.0 mg/kg/day, or 22.5 mg/kg/day.

(c) Experiment: The Human colon cancer strain (KM12C) was subcutaneously transplanted into the back of a nude rat and preliminarily proliferated therein. The proliferated strain was extracted, cut into about 2 to 3 mm square pieces with scissors in physiological saline, and subcutaneously inoculated to the right axillary region of rats of the same strain, 5 to 6 weeks of age, using a transplantation needle. The resulting rats were bred for adaptation at least for 1 to 2 weeks, and divided into a control group and test drug groups at three different doses (3 groups for Compound I-10; and 3 groups for S-1), such that the average tumor volume and the average standard deviation (S. D.) were as equal as possible between the groups (5 to 6 rats per group) (day 0). Then, drug administration was initiated from the next day. Each of the test liquids shown in (a) to (b) above was administered orally to the rats in each of the test drug groups using a sonde for oral administration at a dose of 0.1 ml per 10 g body weight once a day for 14 continuous days. In the same manner as the above, the cancer-bearing rats in the control group were subjected to oral administration of only 0.5% HPMC liquid for 14 continuous days.

The tumor volume of each rat in each group before the initiation of the treatment, on day 3, day 5, day 8 (1 week after), day 11, and day 15 (2 weeks after), i.e., after termination of the administration, was calculated using Equation 1 below, and respective relative tumor volume (RTV) relative to the tumor volume at the time of initiation of the treatment was calculated. In relation to the antitumor effect, the average value of the tumor proliferation inhibition ratio (IR; %) was calculated from the average tumor volume of each treatment group on day 15 (after termination of the treatment) relative to that of the control group on day 15, using Equation 2. Table 1 shows the results. In addition, the occurrence of diarrhea and death were observed through the treatment period of 15 days. The number of occurrences is shown. Along therewith, a weight change ratio was calculated from the body weight of the rats at the time of the termination of the drug administration relative to the body weight of the rats at the time of the initiation of the administration, using Equation 3.

Tumor volume(mm$^3$)=(major axis)×(minor axis)$^2$×½  Equation 1:

Tumor proliferation inhibition ratio(IR, %)=[1−(average tumor volume of treatment group)/(average tumor volume of control group)]×100  Equation 2:

Average weight change ratio(%)=[(average weight on Day 15)−(average weight on Day 1)]/(average weight on Day 1)×100  Equation 3:

(d) Hematological toxicity: All of the rats in relation to which antitumor effects, body weight changes, and macroscopic side effects were observed in Experiment (c) above were anesthetized with ether. Then, an incision was made in the abdomen, and a blood sample was collected from each rat via inferior vena cava with a 5 ml syringe. A coagulation inhibitor was added to each of the collected blood samples, and the white blood cell count, red blood cell count, and platelet count were measured using a hemocytometer. The average value of the rats of the control group, the Compound I-10 groups, and the S-1 groups was calculated, and these average values were compared with each other.

(e) Test results 1: FIG. 2-1 shows the results of the antitumor effects of S-1 and Compound I-10 and changes in the body weight. Compound I-10 of the present invention showed high antitumor effects in a dose-dependent manner over the dosage range of 51 to 77 mg/kg/day. In addition, significant weight loss in mice was not observed, and diarrhea or toxic death in rats was also not observed. This confirms that Compound I-10 of the present invention exhibits a high antitumor effect with reduced toxicity. Similar to the compound of the present invention, S-1, in which gimeracil (a DPD inhibitor) and oteracil potassium (an agent that reduces gastrointestinal toxicity) are added to tegafur (a 5-FU derivative), exhibited an antitumor effect in a dose-dependent manner over the dosage range of 15 to 22.5 mg/kg/day and did not cause a weight loss or diarrhea, which was used as an index of side effects; however, one rat in the 22.5 mg/kg/day group was dead on the last day of the administration.

(f) Test results 2: FIG. 2-2 shows the results of the white blood cell count and the platelet count after administration of S-1 and Compound I-10. The white blood cell count of cancer-bearing rats to which Compound I-10 at a dose of 51 to 77 mg/kg/day was orally administered for 2 weeks was reduced from ¾ to ½ of that of the control group. In contrast, the white blood cell count of rats to which S-1 at a dose of 15 to 22.5 mg/kg/day was administered for 2 weeks, similar to the above, was reduced from ½ to ⅛ of that of the control group. Accordingly, it is clear that Compound I-10 reduced the white blood cell count less, compared to S-1. Further, the platelet count of rats to which S-1 was administered was reduced in a dose-dependent manner; whereas the platelet count of rats to which Compound I-10 was administered was the same as that of the control group. These results reveal that although Compound I-10 of the present invention and S-1 exhibit similar antitumor effects and showed similar results in side effects such as diarrhea and weight loss, Compound I-10 of the present invention has a considerably lower hematological toxicity.

The invention claimed is:

1. A 5-fluorouracil derivative represented by Formula (I) below or a salt thereof:

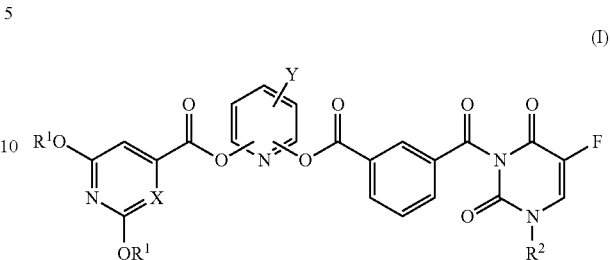

(I)

wherein R$^1$ represents a hydrogen atom or a protecting group of a hydroxy group, R$^2$ represents a lower alkoxy-lower alkyl group or a tetrahydrofuranyl group, X represents a carbon atom or a nitrogen atom, and Y represents a halogen atom or a cyano group.

2. The 5-fluorouracil derivative or a salt thereof according to claim 1, wherein the group represented by the following formula in Formula (I) is:

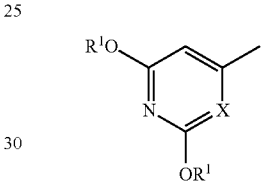

a group represented by:

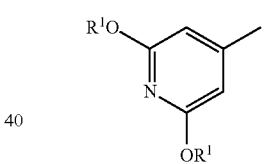

wherein R$^1$ represents a hydrogen atom, an allyl group, or a substituted or unsubstituted benzyl group;

a group represented by:

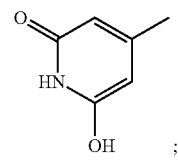

a group represented by:

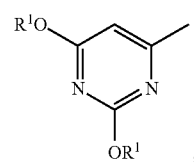

wherein R$^1$ represents a hydrogen atom, an allyl group, or a substituted or unsubstituted benzyl group; or a group represented by:

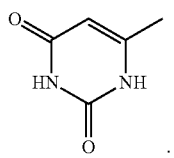

3. The 5-fluorouracil derivative or a salt thereof according to claim 1, wherein $R^1$ represents a hydrogen atom, an allyl group, a benzyl group, an aliphatic acyl group, an aromatic acyl group, or an alicyclic acyl group, $R^2$ represents a lower alkoxymethyl group in which the lower alkoxy moiety has 1 to 6 carbon atoms or a tetrahydrofuranyl group, X represents a carbon atom or a nitrogen atom, and Y represents a fluorine atom or a chlorine atom.

4. The 5-fluorouracil derivative or a salt thereof according to claim 1, wherein $R^1$ represents a hydrogen atom, a benzyl group, an acetyl group, a propionyl group, an isobutyryl group, a pivaloyl group, a benzoyl group, p-chlorobenzoyl, or a cyclopentanecarbonyl group, $R^2$ represents a lower alkoxymethyl group in which the lower alkoxy moiety has 1 to 6 carbon atoms, X represents a carbon atom or a nitrogen atom, and Y represents a fluorine atom or a chlorine atom.

5. The 5-fluorouracil derivative or a salt thereof according to claim 1, wherein $R^1$ represents a hydrogen atom, an acetyl group, or a propionyl group, $R^2$ represents a lower alkoxymethyl group in which the lower alkoxy moiety has 1 to 6 carbon atoms, X represents a carbon atom or a nitrogen atom, and Y represents a chlorine atom.

6. The 5-fluorouracil derivative or a salt thereof according to claim 1, wherein $R^1$ represents a hydrogen atom, an acetyl group, or a propionyl group, $R^2$ represents a lower alkoxymethyl group in which the lower alkoxy moiety has 1 to 6 carbon atoms, X represents a carbon atom, and Y represents a chlorine atom.

7. The 5-fluorouracil derivative or a salt thereof according to claim 1, wherein $R^1$ represents a hydrogen atom, an acetyl group, or a propionyl group, $R^2$ represents an ethoxymethyl group, X represents a carbon atom, and Y represents a chlorine atom.

8. A medicament comprising the 5-fluorouracil derivative or a salt thereof of claim 1 as an active ingredient.

9. A method for treating a cancer comprising administering an effective amount of the 5-fluorouracil derivative or salt thereof of claim 1 to a cancer patient, wherein the cancer is at least one cancer selected from the group consisting of head and neck cancers, gastric cancers, colonic cancers, rectal cancers, liver cancers, gallbladder and bile duct cancers, biliary tract cancers, pancreatic cancers, lung cancers, breast cancers, cervical cancers, renal cancers, and prostatic cancers.

* * * * *